United States Patent
Zon et al.

(10) Patent No.: US 10,736,906 B2
(45) Date of Patent: Aug. 11, 2020

(54) METHOD TO ENHANCE TISSUE REGENERATION

(71) Applicants: CHILDREN'S MEDICAL CENTER CORPORATION, Boston, MA (US); THE GENERAL HOSPITAL CORPORATION, Boston, MA (US)

(72) Inventors: Leonard I. Zon, Wellesley, MA (US); Trista E. North, Newton Center, MA (US); Wolfram Goessling, Chestnut Hill, MA (US)

(73) Assignees: CHILDREN'S MEDICAL CENTER CORPORATION, Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/177,365

(22) Filed: Jun. 9, 2016

(65) Prior Publication Data

US 2016/0354385 A1 Dec. 8, 2016

Related U.S. Application Data

(62) Division of application No. 12/445,986, filed as application No. PCT/US2007/082093 on Oct. 22, 2007, now Pat. No. 9,402,852.

(60) Provisional application No. 60/853,351, filed on Oct. 20, 2006, provisional application No. 60/853,202, filed on Oct. 20, 2006.

(51) Int. Cl.
| | |
|---|---|
| *A61K 31/201* | (2006.01) |
| *A61K 31/404* | (2006.01) |
| *A61K 31/5575* | (2006.01) |
| *A61K 31/557* | (2006.01) |
| *A61K 31/41* | (2006.01) |
| *A61K 31/558* | (2006.01) |
| *A61K 31/5585* | (2006.01) |
| *A61K 31/655* | (2006.01) |
| *A61K 33/14* | (2006.01) |

(52) U.S. Cl.
CPC ........ *A61K 31/5575* (2013.01); *A61K 31/201* (2013.01); *A61K 31/404* (2013.01); *A61K 31/41* (2013.01); *A61K 31/557* (2013.01); *A61K 31/558* (2013.01); *A61K 31/5585* (2013.01); *A61K 31/655* (2013.01); *A61K 33/14* (2013.01)

(58) Field of Classification Search
None
See application file for complete search history.

(56) References Cited

U.S. PATENT DOCUMENTS

| | | | |
|---|---|---|---|
| 6,207,802 B1 | 3/2001 | Zsebo et al. | |
| 6,891,062 B2 | 5/2005 | Oida et al. | |
| 7,625,752 B2 | 12/2009 | Casper et al. | |
| 8,029,780 B2 | 10/2011 | Kollet et al. | |
| 8,241,903 B2 | 8/2012 | Lapidot et al. | |
| 8,367,057 B2 | 2/2013 | Lapidot et al. | |
| 2002/0115586 A1 | 8/2002 | Enikolopov et al. | |
| 2005/0054103 A1 | 3/2005 | Peled et al. | |
| 2005/0074435 A1 | 4/2005 | Casper et al. | |
| 2005/0101599 A1 | 5/2005 | Zeiher et al. | |
| 2005/0153887 A1* | 7/2005 | Lu .......................... | A61K 38/16 435/7.2 |
| 2006/0069018 A1* | 3/2006 | Sakai ................... | A61K 9/1647 514/353 |
| 2006/0147435 A1* | 7/2006 | Moon ................... | A61K 48/005 424/93.21 |
| 2006/0252045 A1* | 11/2006 | Chatterjee-Kishore ..................... | C12Q 1/6876 435/6.13 |
| 2007/0122377 A1 | 5/2007 | Best et al. | |
| 2008/0194024 A1 | 8/2008 | Mays | |

FOREIGN PATENT DOCUMENTS

| | | | |
|---|---|---|---|
| EP | 1563846 | 8/2005 | |
| JP | 2006519250 A | 8/2006 | |
| JP | 2009530408 | 8/2009 | |
| RU | 2205627 | 10/2003 | |
| RU | 2259830 | 10/2005 | |
| WO | 1995/006112 | 3/1995 | |
| WO | 1996/040866 | 12/1996 | |
| WO | 2000/050568 A2 | 8/2000 | |
| WO | 2004-032965 | 4/2004 | |
| WO | 2004/078169 | 9/2004 | |
| WO | 2004078169 A1 | 9/2004 | |
| WO | 2004/113513 A2 | 12/2004 | |
| WO | 2005/044298 A1 | 5/2005 | |
| WO | WO 2005123191 A1 * | 12/2005 | ............. A61K 31/00 |

(Continued)

OTHER PUBLICATIONS

Li et al., "The P2X7 Nucleotide Receptor Mediates Skeletal Mechanotransduction," The Journal of Biological Chemistry vol. 280, No. 52, pp. 42952-42959, Dec. 30, 2005.*

(Continued)

*Primary Examiner* — Jared Barsky
(74) *Attorney, Agent, or Firm* — Nixon Peabody LLP; David S. Resnick

(57) ABSTRACT

The present invention provides for compositions and methods for modulating tissue growth using tissue growth modulators, which are agents that either enhance or inhibit tissue growth as desired by a particular indication by modulating the PG or Wnt signaling pathways, or employing modulators of both PG and Wnt signaling pathways for a synergistic effect or highly selective effect.

15 Claims, 11 Drawing Sheets

(56) References Cited

FOREIGN PATENT DOCUMENTS

| WO | 2006/005153 | 1/2006 |
|---|---|---|
| WO | 2006/078886 | 7/2006 |
| WO | 2006072016 A2 | 7/2006 |
| WO | 2006/086639 | 8/2006 |
| WO | 2007/070964 | 6/2007 |
| WO | 2007/112084 | 10/2007 |
| WO | 2007/112084 A2 | 10/2007 |
| WO | 2008/021475 | 2/2008 |
| WO | 2008/056963 | 5/2008 |

OTHER PUBLICATIONS

Meja et al., "Characterization of the prostanoid receptor(s) on human blood monocytes at which prostaglandin E2 inhibits lipopolysaccharide-induced tumour necrosis factor-alpha generation," Br J Pharmacol, Sep. 1997; 122(1): 149-157.*
Meijer et al., "GSK-3-Selective Inhibitors Derived from Tyrian Purple Indirubins," Chemistry & Biology, vol. 10, 1255-1266, Dec. 2003.*
Koniaris et al., "Liver regeneration." Journal of the American College of Surgeons 197(4):634-659 (2003).
Bos et al., "Prostanoids and prostanoid receptors in signal transduction", Int J Biochem Cell Biol, 36(7):1187-1205 (2004).
Calvi et al., "Prostaglandin E2 (PGE2) Regulates Osteoblastic Jagged1 and Expands Primitive Hematopoietic Cells In Vivo", Blood, American Society of Hematology, 108(11):Abstract 89 (2006).
Hofmeister et al., "Ex vivo expansion of umbilical cord blood stem cells for transplantation: growing knowledge from the hematopoietic niche", Bone Marrow Transplantations, 39:11-23 (2007).
North et al., "Prostaglandin E2 Is a Potent Regulator of Vertebrate Hematopoietic Stem Cell Homeostasis", Blood, 108(11):Abstract 680 (2006).
Wilson et al., "The status of Wnt signalling regulates neural and epidermal fates in the chick embryo", Nature, 411 (6835):325-30 (2001).
Hanson et al., Radiation Research, 103(2):196-203 (1985). "16, 16-dimethyl prostaglandin E-2 induces radioprotection in murine intestinal and hematopoietic stem cells."
Cohn, S.M. et al., Journal of Clinical Investigation, 99(6):1367-1379 (1997). "Crypt stem cell survival in the mouse intestinal epithelium is regulated by prostaglandins synthesized through cyclooxygenase-1."
Feher, I. et al., Nature, 247(442):550-551 (1974). "Prostaglandin E2 as stimulator of haemopoietic stem cell proliferation."
Stier et al., Blood, 99(7):2369-78 (2002). "Notch1 activation increases hematopoietic stem cell self-renewal in vivo and favors lymphoid over myeloid lineage outcome."
Bug et al., Cancer Research, 65(7):2537-2541 (2005). "Valproic acid stimulates proliferation and self-renewal of hematopoietic stem cells."
Galloway et al., Curr Top Dev Biol, 53:139-158 (2003). "Ontogeny of hematopoiesis: examining the emergence of hematopoietic cells in the vertebrate embryo."
Gidali et al., Cell Tissue Kinet., 10(4):365-373 (1977). "The effect of E. type prostaglandins on the proliferation of haemopoietic stem cells in vivo."
Kishi et al., Arch Dis Child, 71(2):153-155 (1994). "Bone marrow suppression induced by high dose valproic acid."
Okunieff et al., International Journal of Radiation Oncology, Biology, Physics, 16(5):1145-1148 (1989). "Effects of hydralazine on in vivo tumor energy metabolism, hematopoietic radiation sensitivity, and cardiovascular parameters."
Sankaranarayanan et al., International Journal of Radiation Biology, 67(1):47-55 (1995). "Radioprotective effects of prostaglandins for chromosomal aberrations and cell killing V79 Chinese Hamster Cells grown as spheroids in vitro and for mouse spermatogonial stem cells and bone marrow cells in vivo."

Desplat et al., Experimental Hematology, 28:741-742 (2000). "Is the COX-2 effect on accelerated hematopoiesis mediated by prostaglandin E2?"
Dupuis et al., Prostaglandins & Other Lipid Mediators, 55:179-186 (1998). "Prostaglandin E2 Stimulates the Growth of Human Blood CD34+ Progenitors."
Gentile et al., Blood, 62(5):1100-1107 (1983). "In Vivo Modulation of Murine Myelopoiesis Following Intravenous Administration of Prostaglandin E2."
Davidson and Zon, Oncogene, 23:7233-7246 (2004). "The 'definitive' (and 'primitive') guide to zebrafish hematopoiesis."
De Jong and Zon, Annu Rev Genet, 39:481-501 (2005). "Use of the zebrafish system to study primitive and definitive hematopoiesis."
Hsia and Zon, Experimental Hematology, 33:1007-1014 (2005). "Transcriptional regulation of hematopoietic stem cell development in zebrafish."
North and Zon, Developmental Dynamics, 228:568-583 (2003). "Modeling human hematopoietic and cardiovascular diseases in zebrafish."
Attar et al., Leukemia, 18:1760-1768 (2004). "Regulation of hematopoietic stem cell growth."
Konturek et al., Journal of Physiology and Pharmacology, 56 (Supp 5):5-31 (2005). "Prostaglandins and ulcer healing."
Guastalla et al., Bull. Cancer, 91:599-108 (2004). "Cyclooxygenase 2 and breast cancer."
Barker et al., Nature Reviews Drug Discovery, 5:997-1014 (2006). "Mining the Wnt pathway for cancer therapeutics."
Janssens et al., Investigational New Drugs, 24:263-280 (2006). "The Wnt-dependent signaling pathways as target in oncology drug discovery."
Goessling et al., Developmental Biology, 320:161-174 (2008). "APC mutant zebrafish uncover a changing temporal requirement for Wnt signaling in liver development."
Goessling et al., Cell, 136:1136-1147 (2009). "Genetic interaction of PGE2 and Wnt signaling regulates developmental specification of stem cells and regeneration."
Kamel et al., "Potential interaction of prostaglandin and Wnt signaling pathways mediating bone cell responses to fluid flow", Journal of Bone and Mineral Research, vol. 21, NR. Suppl. 1, p. S92, Sep. 15-19, 2006.
Kataoka or Kojiro et al., "Prostaglandin E2 receptor EP4 agonist induces Bcl-xL and independently activates proliferation signals in mouse primary hepatocytes", Journal of Gastroenterology, vol. 40, No. 6, pp. 610-616, Jun. 1, 2005.
Lee et al., "Mechanisms involved in prostaglandin E2-mediated neuroprotection against TNF-alpha: possible involvement of multiple signal transduction and beta-catenin/T-Cell factor", Journal of Neuroimmunology, vol. 155, No. 1-2, Oct. 1, 2004.
Schmidt et al., "Influence of prostaglandlin on repair of rat stomach damaged by absolute ethanol", Journal of Surgical Research, vol. 41, No. 4, pp. 367-377, Oct. 1, 1986.
Urakawa et al., "Study of 16, 16-dimethyl prostaglandin E2 for prevention of stress ulcer after hepatectomy of experimental cirrhotic liver and its influence on hepatic regeneration", Database EMBASE [online] 1990.
Okamoto et al., J. Gastroenterol, 39:1-6 (2004). "Molecular and clinical basis for the regeneration of human gastrointestinal epithelia."
North et al., Nature, 447:1007-1011 (2007). "Prostaglandin E2 regulates vertebrate haematopoietic stem cell homeostasis."
Krishnan et al., J Clin Invest, 116(5)1 202-1209 (2006). "Regulation of bone mass by Wnt signaling."
Tseng et al., Chemistry & Biology, 13:957-963 (2006). "The GSK-3 inhibitor BIO promotes proliferation in mammalian cardiomyocytes."
Shao et al., Gastroenterology, 128(4):A146 (2005). "Prostaglandin E2 induces VEGF expresion via the Wnt pathway."
Kanno et al., PNAS, 101 (33):12277-12281 (2004). "Nitric oxide facilitates cardiomyogenesis in mouse embryonic stem cells."
Shevtsov et al., Cell Cycle, Oct. 2006; 5(20): 2295-2300. Epub Oct. 16, 2006.
Walden et al., Radial. Res. Mar. 1987; 109 (3) : 440-448 (abstract only).
Reya et al., Nature 2003, 423, 409-414.

(56) References Cited

OTHER PUBLICATIONS

Samstein, B. et al., J. Am. Soc. Nephrol. 12(1):182-193 (Jan. 2001). "Physiologic and immunologic hurdles to xenotransplantation."
Sprangers B. et al., Kidney Int. 74(1):14-21 (Jul. 2008). doi: 10.1038/ki.2008.135. Epub Apr. 16, 2008. "Xenotransplantation: where are we in 2008?"
Gage, F., Nature. 392(6679 Suppl):18-24 (Apr. 30, 1998). "Cell therapy."
Hoggatt et al., Leukemia. 2010; 24(12): 1993-2002, pp. 1-20.
Pelus, J. Clin. Invest. 70(3):568-578 (1982).
Verma et al., Leuk. Res. 591):65-71 (1981).
Besse et al., Biochimica et Biophysica Acta 1450:444-451 (1999).
Fujino et al., J. Biol. Chem. 277(4):2614-2619 (2002).
Oxford English Dictionry, www.oed.com, accessed 2015.
Stedman's Online Medical Dictionary, wwww.stedmansonline.com, accessed 2015.
Shao et al., "Prostaglandin E2 stimulates the β-catenin/T cell factor-dependent transcription in colon cancer." Journal of Biological Chemistry 280(28):26565-26572 (2005).
Gluckman "Hematopoietic stem-cell transplants using umbilical-cord blood." The New England Journal of Medicine 344(24)1860-1861 (2001).
Hagedorn et al., "Getting more for your marrow: boosting hematopoietic stem cell numbers with PGE2." Experimental cell research 329(2):220-226 (2014).
Hertelendy et al., "Prostaglandin E levels in peripheral blood during labor." Prostaglandins 3(2):223-227 (1973) [Abstract].
Lord et al., "Prostaglandin E2: making more of your marrow." Cell Cycle 6(24):3054-3057 (2007).
Mitchell et al., "Prostaglandins in the human umbilical circulation at birth." BJOG: An International Journal of Obstetrics & Gynaecology 85(2):114-118 (1978).
Porter et al., "Communications between bone cells and hematopoietic stem cells." Archives of Biochemistry and Biophysics 473(2):193-200 (2008).
Hino et al., "Phosphorylation of β-catenin by cyclic AMP-dependent protein kinase stabilizes β-catenin through inhibition of its ubiquitination." Molecular and Cellular Biology 25(20):9063-9072 (2005).
Taurin et al., "Phosphorylation of β-catenin by cyclic AMP-dependent protein kinase." Journal of Biological Chemistry 281(15):9971-9976 (2006).
Robinson et al. "Ex Vivo Expansion of Umbilical Cord Blood." Cytotherapy 7(3): 243-250 (2005).

\* cited by examiner

Key:
- Normal GFP
- Enhanced GFP
- Reduced GFP

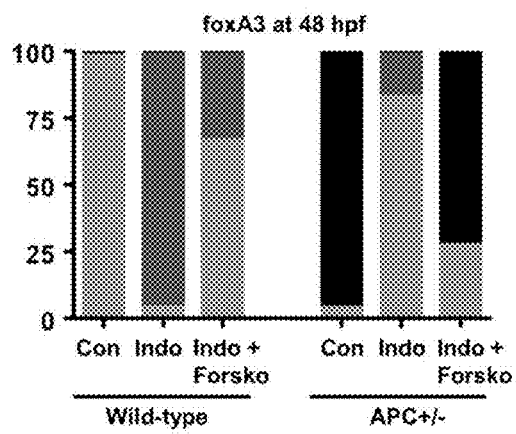
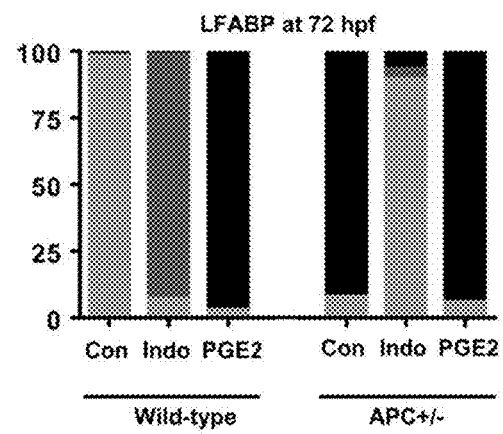
Figure 6A                    Figure 6B
Key:
- Normal foxA3/ LFABP
- Enhanced foxA3/ LFABP
- Reduced foxA3/ LFABP
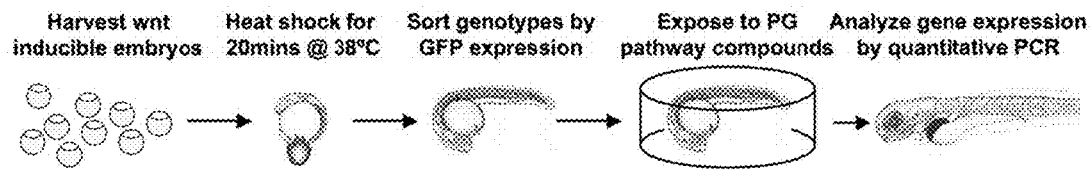
Figure 7A

METHOD TO ENHANCE TISSUE REGENERATION

CROSS REFERENCE TO RELATED APPLICATIONS

This application is a divisional application of U.S. patent application Ser. No. 12/445,986 filed Apr. 17, 2009, now granted, which is a 35 U.S.C. § 371 National Phase Entry of the International Application No. PCT/US2007/082093 filed on Oct. 22, 2007, which designates the United States, and claims the benefit under 35 U.S.C. § 119(e) of U.S. Provisional Patent applications No. 60/853,351, entitled Method to Modulate Hematopoietic Stem Cell Growth, filed on Oct. 20, 2006 and No. 60/853,202, entitled Method to Enhance Tissue Regeneration, filed on Oct. 20, 2006; and also claims the benefit of WO/2007/112084 A2, entitled Method to Modulate Hematopoietic Stem Cell Growth, filed Apr. 26, 2007, each by Leonard I. Zon, Trista E. North and Wolfram Goessling, which applications are incorporated herein by reference in their entirety.

GOVERNMENT SUPPORT

This invention was made with Government support under Grant No. CA103846-02 and DK071940 awarded by the National Institutes of Health. The government has certain rights in this invention.

FIELD OF THE DISCLOSURE

The present embodiments provide for modulators that either enhance or inhibit tissue development or regeneration in vitro, in vivo, and ex vivo. More specifically, for example, modulators that interact with the prostaglandin or wnt signaling pathways may be used to enhance tissue response to regeneration in organs such as liver, hematopoietic stem cells, skin, vessels, and other organs capable of regeneration.

BACKGROUND

Regenerative medicine holds extraordinary potential for the development of therapies which may change the future for those suffering from organ loss due to accident, defect, or disease. Understanding developmental signaling pathways may unlock the promise not only of tissue regeneration, but of cancer inhibition.

For example, in the development of liver tissue, the undifferentiated endodermal germ layer is patterned to form liver, intestine, pancreas, and accessory organs by the action of a variety of signaling pathways. The plasticity of endodermal progenitors at early stages of development, and the mechanisms regulating endodermal cell fate and subsequent organ growth are poorly understood. The liver remains capable of repair and regeneration in the adult, thus further elucidation of the pathways regulating liver development may clarify mechanisms of tissue homeostasis and regeneration. As the progression of disease states involves the reaction of primitive cell programs of proliferation and differentiation, a better understanding of tissue organogenesis may provide targets for pharmaceutical intervention to, for example, inhibit carcinogenesis or, conversely, enhance tissue regeneration.

SUMMARY

The compositions and methods of the present embodiments provide for tissue growth modulators, which are agents that either enhance tissue development and growth or inhibit tissue development as desired by a particular indication. These modulators act by stimulating or suppressing signaling pathways important for tissue growth or regeneration.

For example, wnt signaling may be manipulated to enhance tissue regeneration, particularly liver regeneration, blood repopulation, vessel growth, and wound healing. Activators of the wnt signaling pathway can be used to enhance these processes in both development and regeneration, such a modulator may be a synthetic or soluble wnt ligand, an inhibitor of β-catenin destruction, or a transcriptional co-activator.

Prostaglandin signaling interacts with wnt signaling, and thus may be used to alter wnt activity to modulate development and tissue regeneration. A modulator of the present invention may be a compound that alters prostaglandin signaling or its downstream effectors, and may be used to modify wnt signaling in organ growth and regeneration processes. For example, effectors downstream of the prostaglandin receptor activation such as cyclic AMP, PI3-kinase and protein kinase A can be directly manipulated to exert effects on the wnt signaling pathway.

Modulators of the prostaglandin pathway may also be used as a mechanism to regulate wnt activity, thereby allowing "fine tuning" of growth and regeneration signals. For example, activation of wnt signaling can enhance tissue growth, indomethacin can be used to slow or stop this effect one the desired result has been achieved.

Additionally, modulators of the prostaglandin and wnt pathways may be used synergistically to increase/enhance total wnt activity, while avoiding toxicities of using either high dose or repeated dosing of compound/method to directly activate the wnt pathway. The present invention has confirmed each of these principles in both fish embryos and adults, as well as in adult mammals.

Modulators of the wnt or prostaglandin signaling pathway may be used to enhance liver regeneration after toxic injury, such as acetaminophen poisoning, after surgical resection of tumors or diseased liver tissue, or after resection of a healthy part of the liver for organ donation. These modulators may be administered in a systemic fashion or by direct application to the liver, such as infusion into the portal vein. Furthermore, prostaglandin modifiers may be used ex vivo and in vitro to enhance liver stem cell and hepatocyte growth in culture in preparation for hepatocyte transplants, or in bioartifical liver assist devices for patients with fulminant hepatic failure.

Further more, the modulation of wnt signaling either directly or via manipulation of the prostaglandin pathway could be used in other tissues to enhance organ repair and regeneration, specifically in hematopoietic stem cell growth and homeostasis, in wound healing and repair, in vessel growth and regeneration, and in the repair and regeneration of other organs, such as heart and nervous system.

In general, the compounds of the present embodiments can be applied systemically to the patient, in a targeted fashion to the organ in question, or ex vivo to cells or organ tissue.

Manipulation of the prostaglandin pathway can be accomplished by pharmaceutical measure, such as the targeted administration of activators or inhibitors of various components of the prostaglandin pathway. Alternatively, genes can be targeted through viruses or other devices to the organ of interest to modify the regulation of the prostaglandin pathway.

One embodiment provides a method for promoting tissue cell growth in a subject, comprising administering at least one modulator and a pharmaceutically acceptable carrier.

For example, modulators found to enhance tissue development and adult tissue homeostasis include dimethyl-prostaglandin E2 (dmPGE2) and agents that stimulate the PGE2 pathway.

In another embodiment, the tissue development modulator increases growth by modifying the Wnt pathway. Modulators that enhances tissue growth, such as liver regeneration, hematopoietic stem cell recovery, wound healing, or other organ tissue repair, by directly modifying the wnt pathway include, for example, BIO or LiCl, or other compounds that modulate the wnt pathway at any level or the wnt signaling cascade.

BRIEF DESCRIPTION OF THE DRAWINGS

FIG. 1A compares the size of livers developing in wild-type (normal) and APC+/− mutant zebrafish. FIG. 1B compares the number of GFP positive hepatocytes in APC+/−/LFABP: GFP crosses as determined by FACS analysis. FIG. 1C shows the increase in hepatocyte number in histological sections of APC+/− mutants as compared to control fish. FIG. 1D reflects immunohistochemical analysis of β-catenin at 96 hours post-fertilization (hpf), showing an increase in both cytoplasmic and nuclear staining in APC+/− mutants as compared to wild-type. FIG. 1E illustrates that BrdU incorporation in corresponding liver sections was significantly up-regulated in APC+/− embryos. *=statistically significant difference FIGS. 2A-2B collectively show that increased wnt activity accelerates liver regeneration.

FIG. 5A illustrates the experimental design of determining wnt activity in TOP:dGFP fish. FIG. 5B demonstrates increased wnt activity in the brain following PGE2 administration, and diminished wnt activity after indomethacin exposure. FIGS. 5C and 5D demonstrate similar effects in the developing liver and gut, respectively.

FIGS. 6A-6B collectively show the effect of prostaglandin modulation, cAMP activation and wnt activity on endoderm and liver development. FIG. 6A shows the effects of indomethacin and forskolin, a cAMP activator, in wild-type and APC+/− zebrafish on the endodermal progenitor cell population, demonstrating that downstream mediators of prostaglandin signaling can have similar effects compared to prostaglandins themselves. FIG. 6B shows the effects of PGE2 and indomethacin on liver morphology.

FIGS. 7A-7B collectively show that modulators of the prostaglandin signaling pathway alters the effects of wnt activity on target gene expression. FIG. 7A illustrates one approach to testing prostaglandin pathway modulators using a zebrafish model. FIG. 7B shows the effects of prostaglandin modulators on the expression of wnt target and endodermal genes in wild-type, wnt8, and dkk fish as measured by quantitative PCR.

FIGS. 8A and 8B illustrate approaches to testing prostaglandin pathway modulators in a zebrafish model, by either measuring liver size during regeneration or by analyzing the expression of genes involved in this process. FIG. 8C reveals that inhibition of prostaglandin synthesis decreases wnt target gene expression during liver regeneration.

FIG. 10A and FIG. 10B illustrate approaches to testing prostaglandin pathway modulators in zebrafish carcinogenesis. FIG. 10B depicts the model for testing whether the inhibition of prostaglandin synthesis prevents liver tumor formation in APC+/− zebrafish. FIG. 10C demonstrates the decrease in tumor incidence by inhibition of prostaglandin synthesis in this model.

DETAILED DESCRIPTION

Figure 1A:
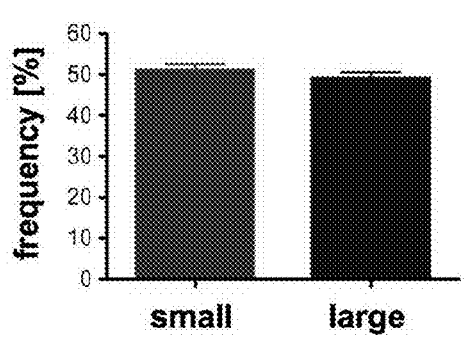
FIGS. 1A-1E collectively show that elevated wnt/β-catenin signaling affects liver size.
Figure 1B:
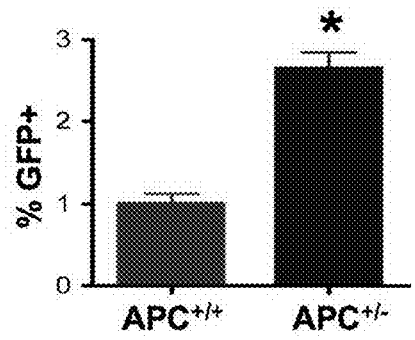
Figure 1C:
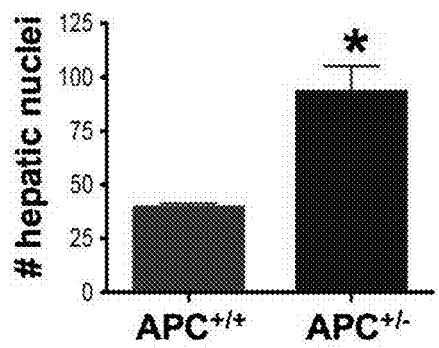
Figure 1D:
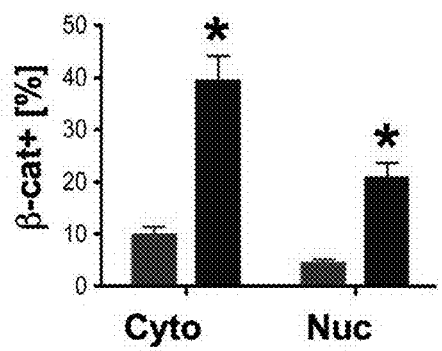
Figure 1E:
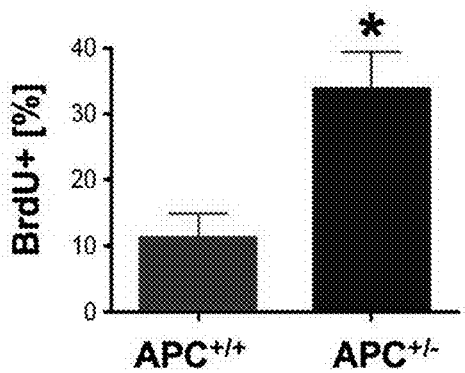
Figure 2A:
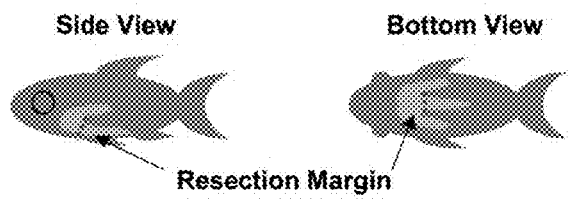
FIG. 2A illustrates the resection margins in adult zebrafish subjected to partial hepatectomy.
Figure 2B:
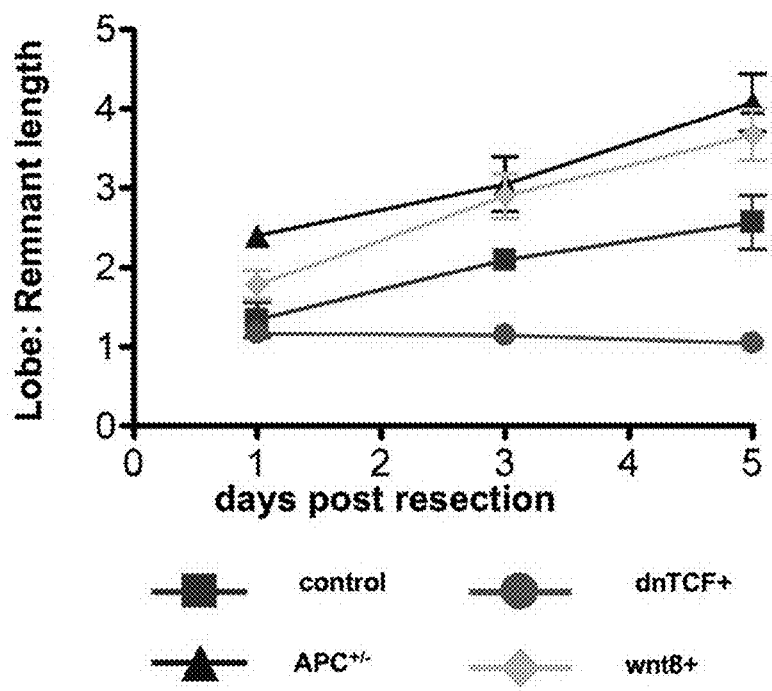
FIG. 2B graphically depicts the results of morphometric analysis of inferior liver lobe regeneration, demonstrating that wnt activation provides a regenerative advantage over wild-type fish, while wnt inhibition diminishes liver regrowth.
Figure 3:
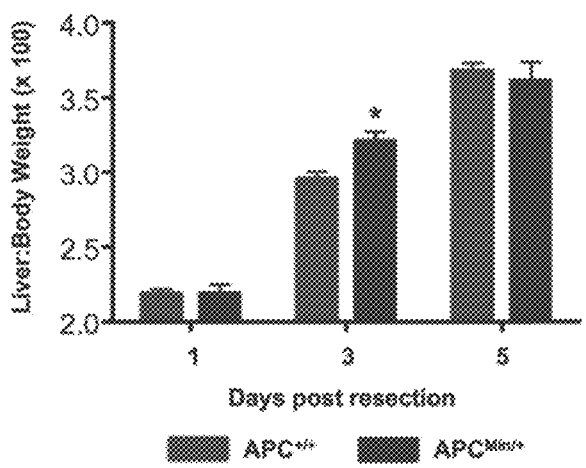
FIG. 3. Wnt-mediated acceleration of liver regeneration is evolutionarily conserved. APC heterozygosity in APCMin/+ mice mediates a growth advantage during liver regeneration following ⅔ partial hepatectomy. *=statistically significant difference FIG. 4. A diagram of the wnt signaling pathway, showing potential sites of interaction with prostaglandin signaling.
Figure 4:
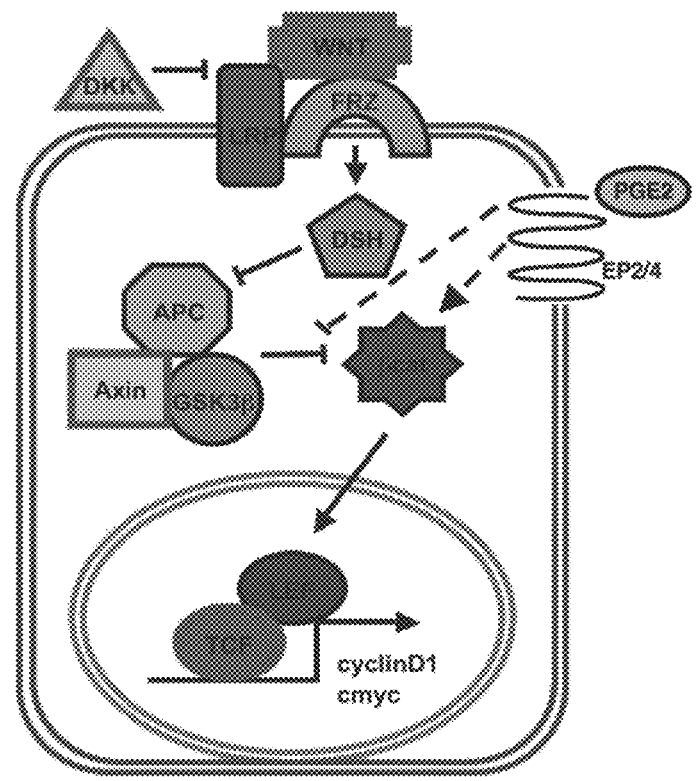
Figure 5A:
FIGS. 5A-5D collectively show the effect of prostaglandin modulation on wnt activity in the developing zebrafish.
Figure 5B:
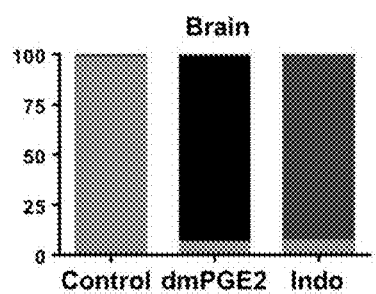
Figure 5C:
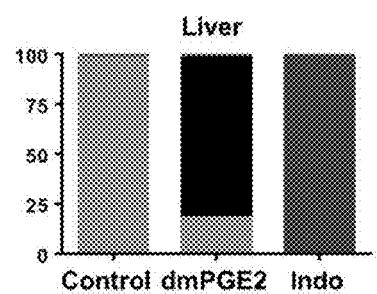
Figure 5D:
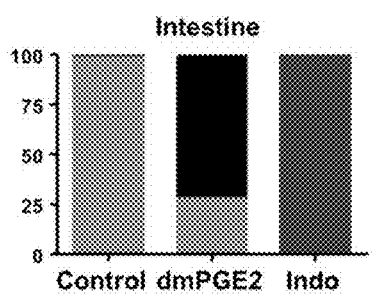
Figure 7B:
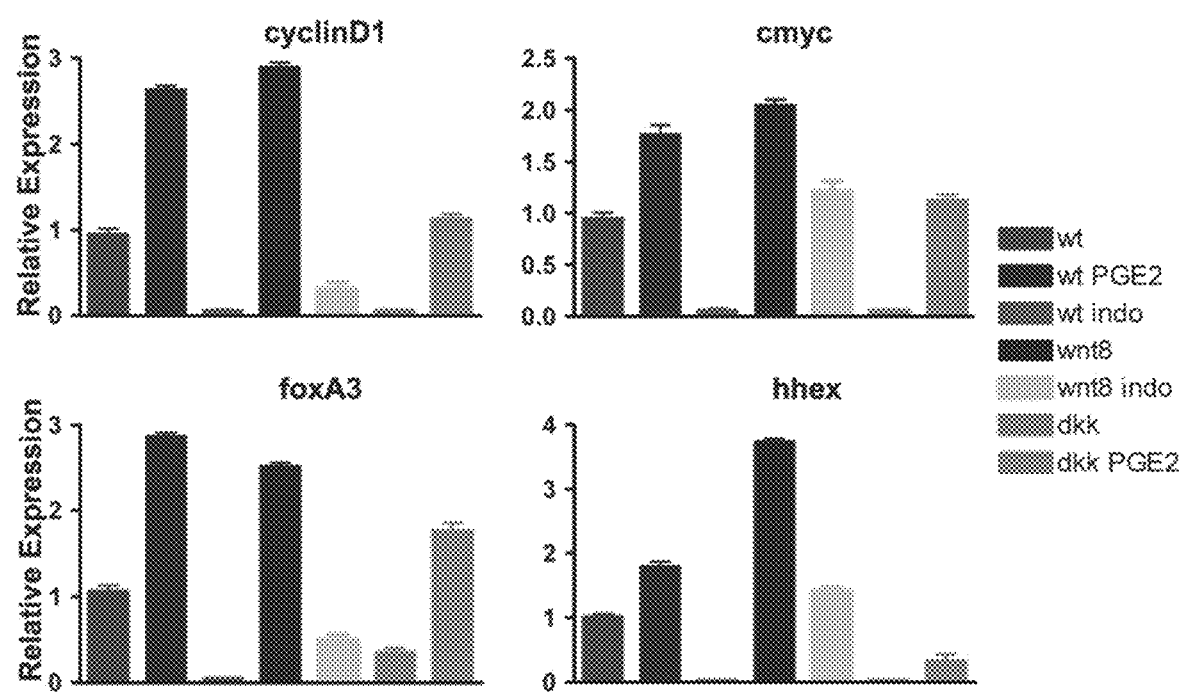
Figure 8A:
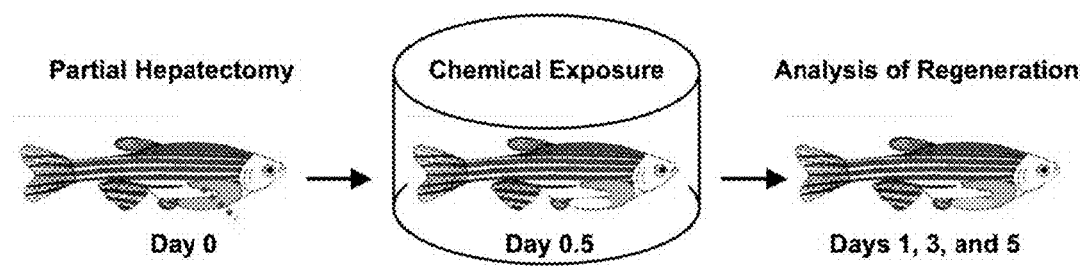
FIGS. 8A-8C collectively show that prostaglandin signaling modifies liver regeneration.
Figure 8B:
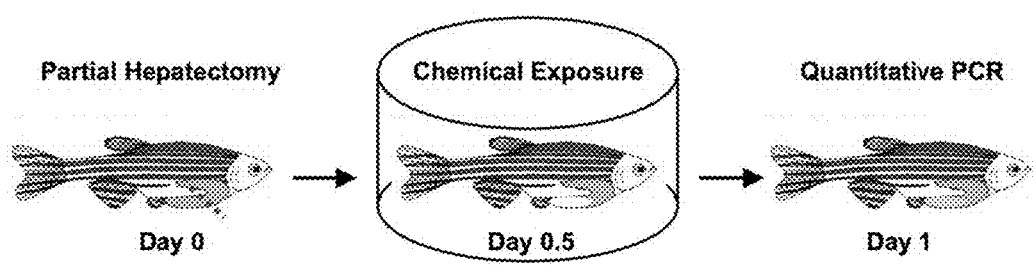
Figure 8C:
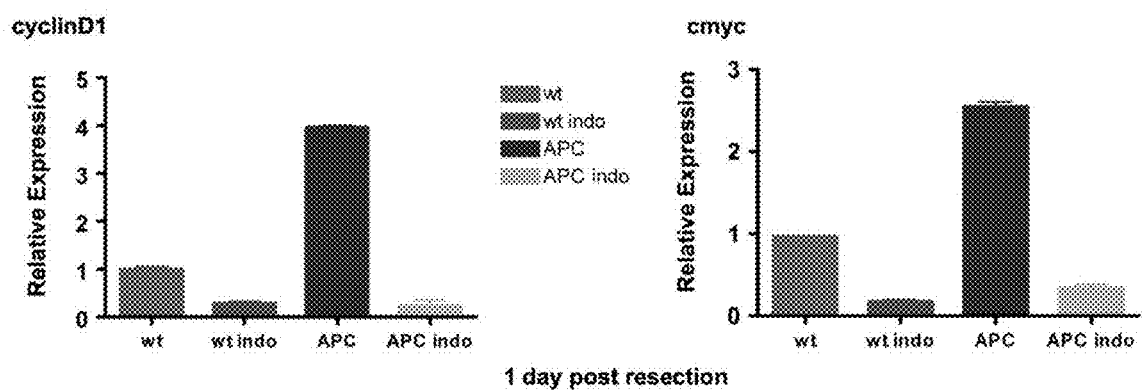
Figure 9A:
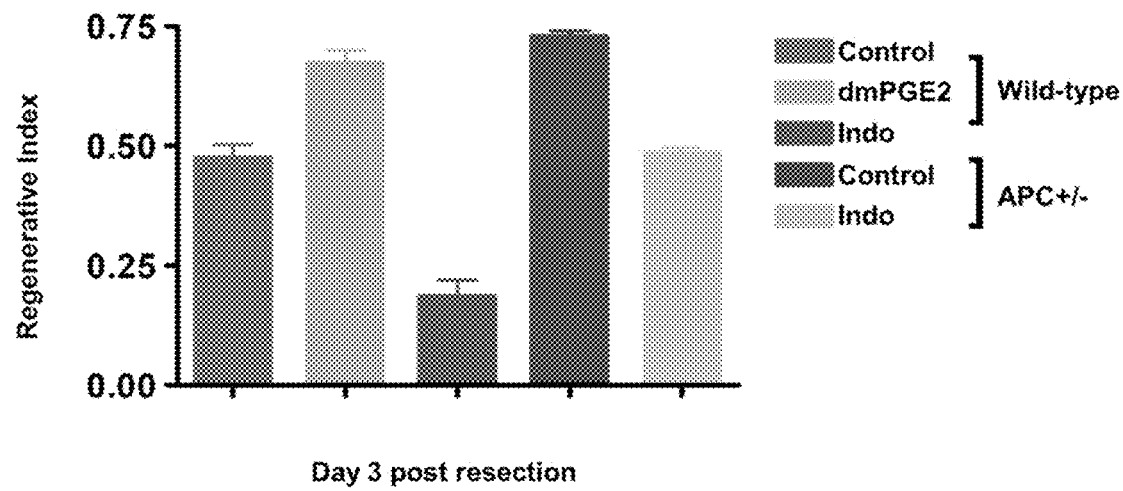
FIG. 9A and FIG. 9B Prostaglandin modulation and wnt activity affect liver regeneration. These figures illustrate how both prostaglandin and wnt activation as well as treatment with components influencing these pathways and downstream targets can affect liver regeneration in zebrafish.
Figure 9B:
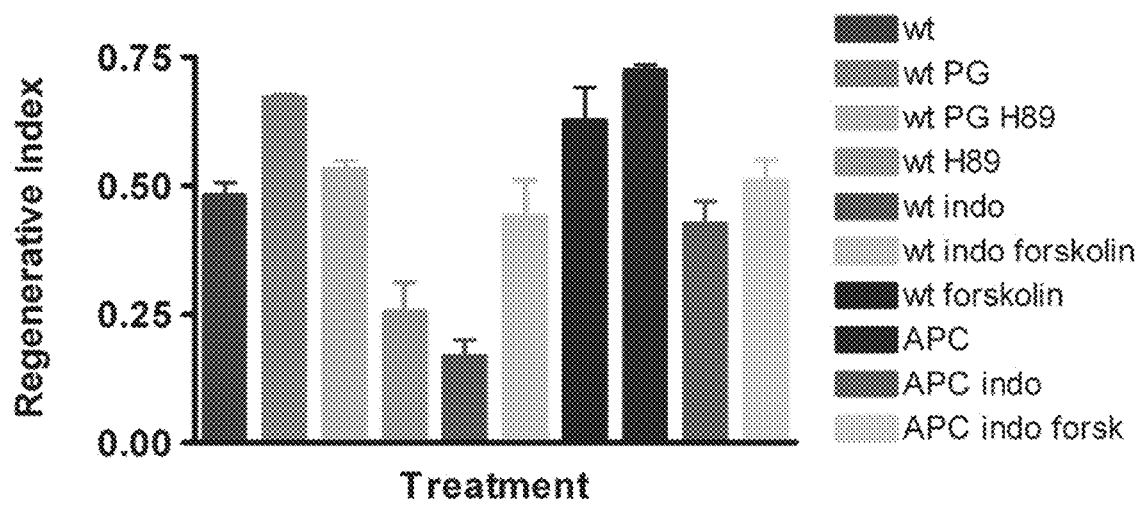

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Developmental signaling pathways hold keys to unlocking the promise of adult tissue regeneration and inhibiting carcinogenesis. The present invention provides insights into the regulation of embryonic and adult hematopoietic stem cell growth. The present invention also provides insights into the regulation of embryonic and adult liver growth, including growth following liver resection.

An embodiment of the present invention provides for manipulation of the genetic interaction between PGE2 and wnt/β-catenin signaling, which regulates developmental specification of stem cells and regeneration. Briefly, prostaglandin (PG) E2 is required for the formation and function of hematopoietic stem cells (HSCs) in vivo, yet its mechanism of action in these cells is not completely understood. North et al., 447(7147) Nature 1007-11 (2007). Clinical observations in patients with APC mutations, a central regulator of the wnt/β-catenin pathway (Cruz-Correa et al., 122(3) Gastroenterology 641-45 (2002)), and in vitro data (Castellone et al., 310 Science 1504-10 (2005)), suggest that the prostaglandin and wnt/β-catenin signaling pathways interact. Wnt signaling positively regulates the homeostatic function of adult HSCs (Reya et al., 423 Nature 409-14 (2003)), but its role in HSC formation has not been examined. In order to demonstrate a direct interaction of PGE2 and the wnt signaling pathway in vivo, TOP:dGFP wnt reporter zebrafish embryos were exposed to a stabilized derivative of PGE2, dmPGE2 (10 µM), and indomethacin (10 µM), a non-selective inhibitor of cyclooxygenases (cox). In situ hybridization for GFP revealed a striking increase in wnt activity throughout the embryo following dmPGE2 exposure (99 observed/111 scored), particularly in the region of the aorta-gonad mesonephros (AGM), where definitive HSCs are formed (12±3.4 vs. 3±1.8 cells). Indomethacin treatment abolished wnt activity in the AGM and markedly decreased GFP expression globally ($^{72}/_{87}$). These results were confirmed by qPCR analysis for GFP, revealing a 2-fold induction of wnt activity in whole embryo extracts following dmPGE2 exposure and indicating the direct influence of PGE2 on wnt signaling activity.

The functional consequences of the PGE2/wnt interaction in HSC formation during embryonic development were analyzed by examining the expression of the HSC markers runx1 and c-myb. Heat shock induction of a canonical wnt ligand, wnt8, at ten somites led to enhanced HSC formation at 36 hours post fertilization (hpf; $^{47}/_{54}$). When wnt8 induction was followed by exposure to indomethacin (10 µM, 16-36 hpf) HSC formation was reduced to or below wild-type levels ($^{43}/_{46}$). These results indicate that PGE2 activity is required for the effects of wnt activation on HSC development.

Inducible negative regulators of wnt activity were used in combination with dmPGE2 treatment to functionally localize the interaction between the PG and wnt pathways. Dkk1 antagonizes the wnt pathway at the level of membrane binding and the initiation of the wnt signaling cascade. Dkk induction in hs:dkk1 transgenic embryos inhibited HSC development ($^{34}/_{49}$). Exposure to exogenous dmPGE2 rescued the dkk1-mediated effect on HSC formation ($^{28}/_{51}$, 10 µM, 16-36 hpf). Axin is a central component of the β-catenin destruction complex and thus a negative regulator of the wnt signaling cascade in the cytosolic compartment. When induced at ten somites, axin severely inhibited HSC formation ($^{47}/_{52}$). Furthermore, this effect could not be overcome by dmPGE2 treatment. Similarly, a dominant-negative form of the β-catenin transcriptional co-activator TCF abolished HSC formation ($^{60}/_{62}$), and no rescue was affected via dmPGE2 exposure. These results indicate that the PG and wnt pathways interact at the level of the β-catenin destruction complex to regulate definitive HSC formation in the embryo.

The wnt pathway can actively enhance HSC proliferation through signaling from the HSC niche as well as within HSCs themselves. PGE2 regulates HSC formation at the level of the vascular niche as well as within the HSCs. North et al., 2007. In order to identify transcriptional programs regulated by the wnt signaling pathway, genes involved in HSC development were analyzed by qPCR. The expression of stem cell markers runx1 and cmyb were significantly enhanced following wnt8 induction, corresponding to the in situ hybridization expression data. Conversely, a significant reduction in runx1 and cmyb was seen in response to dkk1 induction. The general vascular marker flk1, as well as the aorta specific vessel marker ephB2 were each similarly increased in response to wnt8 and diminished following dkk1 induction. These effects on the vascular niche and the HSCs developing therein could be modified by the addition of the appropriate prostaglandin pathway modifier: indomethacin to wnt8, and dmPGE2 to dkk1, respectively. These data suggest that the interaction of PGE2 and wnt, at least in part, affects HSC formation through regulation of the developmental potential level of the hematopoietic niche. Furthermore, analysis of the wnt target gene cyclin D1 by in situ hybridization in the AGM and qPCR indicated that the wnt/PGE2 interaction was also activated in the HSCs themselves, likely influencing their proliferation and self-renewal.

It has been hypothesized that wnt activation regulates HSC self-renewal and repopulation. Wnt activation is also thought to be involved in carcinogenesis, however, making the concept of direct enhancement of wnt signaling problematic. Whether regulation of wnt activity by prostaglandin can effectively modulate HSC homeostasis in the adult, was determined by observing hematopoietic recovery following irradiation in the zebrafish. Previously, it was shown that the PGE2 treatment significantly enhanced regeneration and that the effects on stem and progenitor numbers could be readily detected by ten days post irradiation; lack of PGE2 suppressed stem and progenitor cell proliferation. Wnt activity in the kidney marrow is 2-fold increased following irradiation as analyzed by FACS in TOP:dGFP reporter fish. Furthermore, wnt8 induction from 24 hours-36 hours post irradiation produced a 2.5-fold increase in the stem and progenitor cell population by ten days post irradiation. This effect was significantly diminished following the inhibition of cox by indomethacin. The conservation of the interaction in vertebrate species was shown using a murine model of constitutive wnt activation. APCMin/+ mice have elevated β-catenin levels due to loss of APC function in the destruction complex. These mice exhibit normal differential blood counts at baseline compared to sibling controls. Following 5-FU chemical injury, bone marrow recovery was enhanced in APCMin/+ mice compared to controls. Indomethacin (1 mg/kg every 48 hrs) markedly diminished the proliferative advantage in the APCMin/+ mice. These data confirm that PG and wnt interact to regulate vertebrate hematopoietic homeostasis.

To assess whether prostaglandin levels regulate wnt activity in HSCs, murine transplantation assays were performed utilizing purified HSCs. FACS-isolated cKit+Sca1+ Lineage—(KSL) bone marrow cells were transplanted into lethally irradiated recipients. The recipient mice were treated with the GSK inhibitor BIO (0.05 mg/kg), indomethacin (1 mg/kg and 2.5 mg/kg), or a combination of both to affect both wnt activity and PG levels. CFU-S12 showed a significant 2-fold increase in response to BIO treatment (p=0.03), however, concurrent administration of indomethacin diminished CFU-S number back to baseline levels. These results confirm that PGE2 and wnt directly interact in HSCs.

To determine whether the interaction of PGE2 and wnt/β-catenin signaling is a conserved regulator of stem and progenitor cell populations in other tissues, endodermal and hepatic progenitor cells were examined during zebrafish development. Zebrafish embryos exposed to indomethacin exhibited decreased foxA3 expression, a marker for endodermal progenitor cells ($^{67}/_{71}$). In particular, the developing liver bud was markedly decreased, resulting in a smaller liver at 72 h.p.f. ($^{51}/_{56}$), as detected by expression of liver fatty acid binding protein (lfabp). Addition of dmPGE2 resulted in an expanded foxA3 population with an increased liver anlage ($^{75}/_{83}$) and increased liver size ($^{88}/_{92}$), revealing a novel role for PGE2 signaling in endoderm development. This finding is supported by the detection of various components of PGE2 signaling in foxA3 positive cells.

Wnt signaling has been shown to be required for endoderm and liver formation. The APC mutant zebrafish to model constitutive activation of the wnt signaling pathway, was used to characterize the effects of the wnt/PG interaction in foxA3+ endodermal progenitors at 48 hpf. APC+/− embryos have enhanced foxA3 expression and and an increased liver bud ($^{88}/_{93}$) as well as increased liver size ($^{68}/_{75}$) compared to wild-type siblings. Indomethacin caused a decrease in foxA3 positive progenitor cells ($^{33}/_{39}$) and liver size ($^{61}/_{67}$) in APC+/− embryos, comparable to untreated wild-type controls, while dmPGE2 enhanced both endodermal progenitors ($^{47}/_{54}$) and liver size ($^{75}/_{81}$) excessively. Use of the heat-shock inducible transgenic lines confirmed that as in HSCs the interaction of the PG and wnt pathways during endodermal development occurs at the level of the destruction complex. qPCR revealed that both markers of endodermal (foxA3) and hepatic progenitors (hhex) are regulated, suggesting that the interaction of PG and wnt is involved at different progenitor populations during endoderm development. Insulin expression is not affected by modulation of the PG pathway, indicating that the PG/wnt regulation is not a general regulator of different endodermal lineages. Both cyclinD1 and cmyc were co-regulated by wnt and prostaglandin during development which may indicate that PGE2 exerts its effects on stem cells through enhanced cell cycling and proliferation.

The continued importance of the PG/wnt pathways in adult liver homeostasis was demonstrated clearly using a liver resection model in the zebrafish. Following ⅓ partial hepatectomy, the zebrafish liver regenerates within five days to seven days. This process is accelerated in APC+/− fish. Treatment with indomethacin from 6 hours to 18 hours post resection significantly diminished the regenerative index in both wild-type and APC mutant fish. Immunohistochemistry for β-catenin reveals enhanced nuclear staining in APC+/− fish post resection. Indomethacin caused a decrease in overall β-catenin levels, however, and the absence of nuclear β-catenin in both wild-type and APC+/− fish.

The mechanism by which PGE2 affects β-catenin levels and to demonstrate a conserved role of this interaction in mammalian liver regeneration were further elucidated by performing partial hepatectomies in wild-type and APC-Min/+ mice. Here, APC mutation caused increased total and nuclear β-catenin levels, particularly in the periportal region. Exposure to indomethacin (2.5 mg/kg bid sq) decreased β-catenin levels significantly in both genotypes. Cell culture studies have suggested that PGE2 may enhance b-catenin levels by phosphorylation and inactivation of GSK3b through activation of adenylyl cyclase and protein kinase A (PKA); IHC for P-GSK3b (at serine 9) revealed decreased amounts after indomethacin exposure in both wild-type and APC+/− mice. These findings were confirmed by western blot. β-catenin may cause increased cell proliferation through its target cyclin D1. Cyclin D1 levels and resultant cell proliferation as measured by BrdU incorporation were increased in APCMin/+ mice and markedly diminished after indomethacin exposure.

The functional interaction of signaling processes in the zebrafish, down stream from PG, was explored by increasing camp production using forskolin and inhibiting PKA with H89. In both HSCs and endodermal progenitors, forskolin exposure had similarly enhancing effects as dmPGE2. Forskolin was able to rescue the inhibitory effects of indomethacin in both wild-type and wnt8 transgenic fish. Inhibition of PKA by H89 reduced the increased HSC formation induced by dmPGE2. Furthermore, the rescue of dkk effects by dmPGE2 was eliminated by H89. These data suggest that PGE2 acts through activation of camp and PKA and subsequent inactivation of GSK3b to enhance β-catenin levels in various stem and progenitor populations Another embodiment of the present invention provides for the role of wnt/β-catenin signaling in the processes of liver development and growth. Briefly, embryos heterozygous for the adenomatous polyposis coli gene (APC+/−), a critical regulator of wnt signaling, developed enlarged livers. Conversely, APC−/− embryos failed to specify liver. Elevated wnt signaling and increased intracellular β-catenin mediated both APC liver phenotypes. Using transgenic zebrafish that expressed inducible activators and repressors of wnt/β-catenin signaling, the requirement for wnt during embryogenesis was shown to be biphasic: suppression of wnt signaling was required following gastrulation for hepatic cell fate specification; conversely, activation of wnt signaling was necessary for normal liver growth. Liver resections were preformed in both zebrafish and mice to assess the functional requirement of wnt signaling in hepatic regeneration. Intriguingly, APC heterozygotes demonstrated accelerated liver regeneration, while inhibition of wnt signaling severely diminished regrowth. The present invention reveals an evolutionary conserved role for wnt/β-catenin signaling in endodermal organ specification, hepatocyte growth and liver regeneration, which has implications for regenerative medicine.

Another embodiment of the present invention provides for the role of the prostaglandin signaling pathway as a potent modifier of liver growth. Incubation of zebrafish embryos with cox1-, cox2-, or dual-specific inhibitors (e.g., indomthacin) caused a marked reduction in liver size by 72 hours post-fertilization compared to controls. Conversely, exposure to dimethyl-prosaglandin E2 (dmPGE2) enhanced liver development. Morpholino knock-down of either cox1 or cox2 similarly inhibited growth, but such growth was rescued fully by exposure to exogenous dmPGE2. Adult zebrafish subjected to partial hepatectomy and exposed to indomethacin showed significantly reduced liver regrowth compared to controls. Cox inhibition also prohibited wound healing. In contrast, exposure to dmPGE2 following resection led to enhanced liver regrowth with noted increases in liver vascularity compared to untreated fish. More rapid would healing was also observed in dmPGE2-treated fish. Similar studies in zebrafish demonstrated that dmPGE2 could enhance kidney marrow repopulation following injury. Hence, regulation of the prostaglandin pathway may impact repair/regrowth in a variety of tissue types such as cardiac, bone and wounded tissue.

The undifferentiated endodermal germ layer is patterned to form liver, intestine, pancreas, and accessory organs by the action of signaling pathways. Cui et al., 180 Dev. Biol. 22-34 (1996); Zaret, 3 Nat. Rev. Genet. 499-512 (2002). Wnt signaling through its main transcriptional mediator β-catenin plays an important role in controlling tissue patterning, cell fate decisions, and proliferation in many embryonic contexts, including the development and differentiation of organs. Clevers, 127 Cell 365-69 (2006). In the absence of Wnt signaling, β-catenin is phosphorylated by the action of a destructive complex of Axin, APC, and Glycogen Synthase Kinase (GSK) 3β, and targeted for degradation. Binding of Wnt ligand to surface receptors allows β-catenin to accumulate in the cytoplasm and translocate to the nucleu, where is modulates gene expression.

Genetic mutations in several components of the Wnt/β-catenin signaling pathway are frequently detected in gastrointestinal neoplasia. Most prominently, patients carrying mutations in the APC gene develop colon cancer at a very young age. Kinzler et al., 251 Sci. 1366-70 (1991). Children with APC mutations are 1000-times more likely to develop hepatoblastoma, an embroyonal form of liver cancer. Hirschman et al., 147 J. Pediatr. 263-66 (2005). Mutations in (3-catenin as well as AXIN-1 and -2 are found in hepatocellular carcinoma (HCC) (Taniguchi et al., 21 Oncogene 4863-71 (2002). Based on the prevalence of defects in Wnt pathway components found in both primitive and differentiated hepatic neoplasms, it is likely that β-catenin signaling regulates several aspects of liver development.

The liver is derived from anterior endodermal progenitor cells during embryogenesis. Following convergence of the endodermal progenitors to the midline, the proliferation and specification of the endodermal rod is initiated. In the zebrafish embryo, endodermal progenitors fated to become liver can be identified at 22 hours to 24 hours post fertilization (hpf) as a thickening in the anterior endoderm. Field et al., 253 Dev. Bio. 279-90 (2003). As the endoderm develops further, the liver primordial appears as a prominent bud extending to the left from the midline over the yolk sac. Between 28 hpf and 30 hpf, the transcription of liver-specific genes is initiated within cells specified to become liver. The liver is fully developed by 48 hpf and expresses mature liver-specific genes such as liver fatty acid binding protein (LFABP). Her et al., 538 FEBS Lett 125-33 (2003). Hepatic growth continues as the zebrafish liver expands anteriorly and leftward. The mechanisms by which liver specification, budding, and growth in the vertebrate embryo are initiated and controlled appear to be highly conserved across vertebrate species.

The requirement for Wnt signaling in the development of the endoderm was described initially in *C. elegans*, and is evolutionarily conserved. Lin et al., 83 Cell 599-609 (1995). An analysis of the role of Wnt/β-catenin signaling in vertebrate endodermal development was slowed by early embryonic lethality of mice with homozygous deletion of β-catenin. Haegel et al., 121 Devel. 3529-37 (1995). APC-Min homozygous mutant mice are also embryonic lethal, although heterozygotes are viable and develop neoplasia as adults. Su et al., (1992). In *Xenopus*, wnt is required during gastrulation for endodermal patterning. Heasman et al., (2000). Through inducible inactivation of β-catenin, Wnt/β-catenin signaling was shown to be required for the development of the intestine and formation of intestinal architecture. Ireland et al., (2004). Additionally, Wnt-dependent regulation of intestinal crypt anatomy is maintained in the adult. Pinto et al., (2003). Recent studies on Wnt signaling in liver development have produced seemingly contradictory findings. Emerging data in *Xenopus* suggest that repression of wnt in early endodermal progenitor cells is needed to allow liver specification to occur. In contrast, the zebrafish wnt2b mutant, prometheus, reveals a requirement for mesodermally derived Wnt signals in regulating liver growth. Ober et al., (2006). Homozygous prometheus mutants are viable and eventually develop a liver. This suggests that liver progenitors can be correctly specified in the absence of wnt2b, but that lack of mesodermal wnt2 signaling impairs the initial wave of liver growth. It is unknown whether other wnt factors compensate for the lack of wnt2b in liver specification and development, or if wnt is not required for later phases of hepatocyte proliferation.

Zebrafish possessing mutation in APC were identified previously through TILLING (targeting induced local lesions in genomes). Hurlstone et al., 425 Nature 633-37 (2003). Although APC+/− mutants dies by 96 hpf, APC+/− fish are viable and have increased susceptibility for the development of spontaneous gastronintestinal neoplasia. Haramis et al., (2006). Liver tumors arising in APC+/− mutant zebrafish resemble hepatoblastomas, implying the APC mutation leads to a defect in wnt-regulated differentiation of hepatic progenitors.

Utilizing APC mutant and transgenic zebrafish expressing inducible activator and repressors of wnt/β-catenin signaling, the present invention provides for the characterization of the temporal requirement of wnt/β-catenin signaling during embryonic development and in mediating tissue homeostasis in the adult. There is a differential effect of APC loss on liver development, mediated by changing temporal requirements of wnt signaling during hepatogenesis. Wnt activation influences endodermal progenitor fate decisions resulting in increased liver and intestinal development at the expense of pancreatic tissue formation. Through the creation of a zebrafish model for partial hepatectomy, the present invention demonstrates a requirement for wnt during liver regeneration in vivo. Additionally, the present invention shows that the role of elevated wnt signaling in enhancing the regenerative process is conserved in zebrafish and mice. These data demonstrate that Wnt/β-catenin signaling is required and highly regulated during several aspects of liver development and maintains a central role in organ homeostasis. Hence, the present invention provides for methodology for the transient upregulation of Wnt signaling, which may serve as an attractive mechanism to enhance liver regeneration in mammals and humans.

The differential effects of APC loss on liver organogenesis was elucidated by crossing APC+/− zebrafish into a LFABP: GFP fluorescent reporter line, and assessing liver development by fluorescence microscopy. By 72 hpf, APC+/− embryos showed a dramatic increase in liver size (265/297) compared to wild-type siblings. In contrast, no LFABP expression could be detected in homozygous APC−/− mutant embryos (134/134) at any stage of development. To ensure that the observed phenotypic changes in liver development were not simply due to variation in the expression of LFABP, in situ hybridization for sterol carrier protein and transferring were performed, yielding similar results.

Flow cytometry analysis of GFP+ cells in progeny of APC+/−: LFABP:GFP incross revealed a three-fold increase in hepatocyte number in APC+/− embryos, and confirmed the absence of GFP+ hepatocytes in APC+/− mutants. Hepatocyte nuclei counts in corresponding histological sections corroborated the differential effects of APC loss on liver development; ACP−/− embryos showed a complete absence of hepatocytes by histological analysis, while APC+/− embryos exhibited a significant increase compared to wild-type. No change in the overall cellular morphology was observed between wild-type and APC+/− samples.

As APC co-regulates the availability of β-catenin in the nucleus, the cellular content and localization of β-catenin within hepatocytes in wild-tyoe and APC+/− embryos was examined at 72 hpf by immunohistochemistry (IHC). Wild-type livers exhibited primarily membrane-bound β-catenin. In the livers of APC+/− embryos, β-catenin staining was markedly increased, with 4-fold enhanced cytoplasmic and 5-fold increased nuclear staining. Wnt/β-catenin signaling is known to mediate effects on the cell cycle, cellular proliferation and apoptosis in a variety of tissues. Alonso & Fuchs, 17 Genes Devel. 1189-1200 (2003); Pinto et al., 17 Genes Devel. 1709-13 (2003); Reya et al., 243 Nature 409-14 (2003). To determine whether the increase in total hepatocyte number in the APC+/− embryos was due to increased proliferative activity, BrdU incorporation was examined at 72 hpf. A significant increase in the percentage of BrdU positive cells per liver was seen in APC+/− embryos compared to wild-type. Similar results were seen with PCNA staining.

Although the absence of liver development precluded an assessment of β-catenin distribution in hepatocytes of embryos, the adjacent endodermal tissue exhibited intense staining for β-catenin along the entire length of the gastrointestinal tract and BrdU incorporation was seen in nearly every cell. Aberrant wnt signaling due to APC loss in the intestine and developing brain leads to a block in differentiation and eventually apoptosis. Chenn & Walsh, 297 Sci. 365-69 (2002); Sansom et al., 18 Genes Devel. 1385-90 (2004). To further assess why the APC+/− embryos fail to develop hepatocytes despite the presence of abundant wnt signaling, TUNEL staining was evaluated in histological sections of APC+/− embryos. Hugh levels of TUNEL-positive apoptotic cells were found along the entire length of endoderm, including the area where liver differentiation failed to occur. Capsase activity, a marker of apoptosis, was twice as high in APC−/− embryos as wild-type. These data suggest that the lack of liver in the APC+/− mutants is due to death of endodermal progenitors.

Increased levels of β-catenin are responsible for the differential liver phenotypes in APC mutants. An intriguing finding was that progressive loss of APC did not have a linear effect on liver size. To demonstrates that β-catenin caused both the enlarged liver in the APC−/− embryos and failure of liver specification in APC+/− mutants, β-catenin levels were reduced by a morpholino antisense oligonucleotide (MO) strategy. MOs against the start sight of zebrafish β-catenin (Lyman Gingerich et al., 286 Devel. Bio. 427-39 (2005)) were injected into the progeny of an APC+/− incross at the one-cell stage. By using a low concentration of the MO (40 µM), injected embryos were able to successfully progress through gastrulation, and no effects on overall gross morphology were noted compared to control MO-injected embryos.

Targeted knockdown of β-catenin led to a dramatic shift in the districbution of the liver phenotypes. The majority of embryos (74%) displayed a normal liver, and subsequent genotyping revealed that this population included both wild-type and APC+/− embryos. Some APC+/− embryos (15%) still exhibited an enlarged liver, likely reflecting an insufficient functional knock-down of β-catenin caused by the low MO dosing. Of APC+/− embryos injected with MO that survived until 72 hpf, 43% now had evidence of LFABP expression; these embryos still exhibited severe developmental defects, however, and were not viable beyond 120 hpf. These data suggest that β-catenin levels alone are sufficient to cause both liver phenotypes, indicating that the wnt/β-catenin pathway as mediator of these effects. This conclusion is supported by the fact that knockdown of canonical wnt2b, wnt3, and wnt8 resulted in reduced liver size.

Wnt/β-catenin signaling effects the endodermal progenitor population. Inducible transgenic zebrafish expressing activators or repressors of wnt signaling were employed to determine at which stage of embryonic development wnt signaling effects endodermal differentiation and liver size. hs:wnt-GFP fish express the wnt ligand wnt8 under the control of a heat-shock-inducible promoter, while hs:dkk-GFP and hs:dnTCF-GFP allow inhibition of wnt/β-catenin signaling either at the level of the frizzled receptor or the nuclear transcript or the nuclear transcription complex, respectively. Global induction of wnt8 prior to the tail bud stage of development (10 hpf) caused severe disruption of gastrulation and overall embryonic patterning resulting in growth arrest or death by 24 hpf. Between the 1-somite and 5-somite stages, wnt activation caused significant cardiac edema, reduced body length and absence of liver formation in embryos surviving until 72 hpf, reminiscent of APC−/− mutants. Heat-shock induction of wnt8 from 10-18 somites resulted in markedly enlarged livers compared to heat-shocked wild-type controls. In addition to the overall increase in organ size, 50% of livers heat-shocked at 10 somites failed to segregate entirely from the endodermal rod, resulting in increased liver-specific gene expression at the midline, and a posterior extension of liver cells; this phenotype was confirmed by confocal microscopy and histological sectioning. Transient wnt activation at time points between 24-hpf and 36-hpf produced moderate effect on liver size at 72 hpf. Similarly, the effect of wnt inhibition on liver development caused by the induction of dkk or dnTCF was most significant from 10-18 somites, and more modest later in embryonic maturation. Global inhibition of wnt/β-catenin signaling prior to the 5 somite stage resulted in early embryonic lethality.

The expression of liver-specific transcripts such as LFABP begins at ~44 hpf, and the segregation of the endodermal tubes into a region fated to become liver is thought to be established by 22 hpf. The results obtained in the heat-shock assays suggested that the wnt-mediated effects on liver development originated prior to the formation of the mature organ, at or slightly before the stage at which the fate of endodermal progenitors is determined. To investigate the effect of wnt activation on the endodermal progenitor cell population, the expression of the pan-endodermal marker foxA3 was analyzed after heat-shock induction of wnt8. A significant increase in the size of the liver bud was observed at 48 hpf following heat activation at 10 somites; a decrease in the size of the pancreatic anlage was also seen, while the effects of later wnt8 induction (after 24 hpf) were less notable. wnt8 activation also had a dose-dependent effect on endodermal progenitors: compared to controls, heat-shock for 5 minutes, 20 minutes, and 60 minutes at the 18-somite stage resulted in progressive enlargement of the liver but at the expense of pancreatic tissue.

β-catenin activation in APC mutants resulted in altered endodermal fate. The heat-shock experiments suggested that the wnt-mediated enhancement of hepatocyte number occurs at the level of endodermal progenitor cells. To evaluate the effects of progressive APC loss on endodermal progenitors, expression in progeny of an APC+/− incross was examined at 48 hpf. Compared to wild-type, APC+/− embryos exhibited increased liver and decreased pancreatic buds. The phenotype was confirmed in vivo by confocal microscopy of APC; gut:GFP incrosses, and by FACS analysis at 48 hpf. The APC+/− embryos failed to exhibit clear patterns of endodermal organization at 48 hpf and had reduced numbers of gut:GFP+ progenitors by FACS analysis, implying that neither definitive organ nor endodermal progenitor cell expansion occurred.

As all populations of endodermal progenitors appeared to be affected by APC loss or wnt activation, mature endodermal organs were examined for consequences of this early alteration in development. Insulin and trypsin expression, indicative of endocrine and exocrine pancreas differentiation, respectively, were decreased in APC+/− embryos at 72 hpf. In APC−/− mutants, trypsin expression was virtually undetectable; insulin expression, although reduced, could still be observed. The effect of APC loss on differentiated intestine as marked by expression of intestinal fatty acid binding protein (IFABP) was similar to the liver: APC+/− embryos had increased IFABP staining compared to wild-type, while APC−/− embryos failed to express IFABP. Induction of wnt8 at 10 somites had similar effects on each endodermal organ but resulted in more disorganized patterning, especially of the pancreas. These data demonstrate that nascent wnt/β-catenin signaling regulates endodermal development prior to organ specification, and that this effect mediates a shift in the differentiation of endodermal progenitors into liver at the expense of pancreatic tissue. In addition, excess wnt/β-catenin activation at tailbud and early somite stages leads to a failure of endodermal specification and proliferation that results in elevated endodermal cell death and the inability to develop mature endodermal organs.

Wnt/β-catenin signaling enhances hepatocyte growth. To determine if wnt/β-catenin signaling also mediates an effect of the growth of differentiated hepatocytes, wnt8 expression was induced at 48 hpf. This resulted in a 2-fold increase in liver size both by confocal microscopy of LFABP:GFP fish and in GFP+ cells by FACS at 72 hpf. As specified hepatic progenitor cells begin to proliferate the liver expands dramatically in size: between 72 hpf and 120 hpf the number of liver cells increases 2-fold to 3-fold in wild-type embryos. By FACS analysis, wnt8-induced embryos still possess increased number of GFP+ hepatocytes at 120 hpf, although this difference is no longer readily apparent by gross examination of LFABP expression. Heat-shock induced inhibition of wnt signaling at 48 hpf demonstrated that wnt was required for optimal liver growth; both dkk and dnTCF embryos had reduced liver size compared to controls by in situ hybridization at 72 hpf. These data demonstrate that wnt signaling continues to be important in the proliferation of differentiated hepatocytes.

Wnt/β-catenin signaling is activated and required during liver regeration. The vertebrate liver is a dynamic organ that can repair limited damage throughout its lifetime. A model of liver regeneration in the zebrafish was developed in order to evaluate the role of wnt/β-catenin signaling in the maintenance of liver homeostasis in the adult. Adult zebrafish have a trilobar liver; after ⅓ partial hepatectomy by removal of the inferior lobe, >95% of wild-type zebrafish recover immediately and their liver regenerates entirely within seven days. In wnt/β-catenin reporter fish (TOP:dGFP), GFP fluorescence could be observed at the liver resection margin at 24 hours post resection (hpr), indicating activation of the wnt signaling pathway during the early stages of liver regeneration. This correlated with increased nuclear β-catenin in regenerating livers compared to sham-operated controls.

To determine whether excess wnt activation provides a regenerative advantage, wnt8 expression was induced by heat-shock from 6 hpr-18 hpr. This treatment caused notable acceleration in liver growth compared to wild-type controls at 3 hpr. Similarly, the APC+/− mutants displayed enhanced regenerative capacity compared to controls. Use of dnTCF transgenics revealed that both liver regeneration and wound healing were severely impaired and demonstrated that wnt/β-catenin signaling was requied for liver regeneration in zebrafish. Histological analysis confirmed these findings at all stages of regeneration. Nuclear and cytosolic β-catenin levels as well as PCNA staining were increased in zebrafish with elevated wnt signaling and enhanced regeneration. These experiments highlight the persistent important of wnt/β-catenin signaling in liever homeostasis and growth throughout the lifetime of the organism.

Importantly, elevated β-catenin signaling can enhance mammalian liver regeneration. To test that prediction that increased levels of wnt/β-catenin signaling could confer a conserved regenerative advantage following partial hepatectomy in mammals, liver resections were preformed in APCMin/+ and wild-type mice. After standard ⅔ partial hepatectomy, an assessment of the liver weight:body weight ratios revealed as increased regenerative capacity in the APCMin/+ mice compared with controls which was most notable during the early stages of hepatic regrowth. In APCMin/+ mice, β-catenin levels were increased at baseline, primarily located around the portal tracts, and increased significantly during the early phases of liver regeneration. Data from the APCMin/+ mice demonstrates that wnt activation enhances the kinetics of liver regeneration, and additionally suggests that pharmacological manipulation of wnt/β-catenin signaling would accelerate hepatic regeneration following injury.

Indication of the molecular mechanisms controlling liver development both sheds light on the biological basis of hepatic tumor formation and provides targets for therapeutic manipulation. As defects in wnt/β-catenin signaling are prevalent in both primitive and differentiated hepatic neoplasms, the present invention provides for role of wnt signaling in regulating both liver specification and growth. Through analysis of transgenic zebrafish expressing activators and repressors of wnt signaling, as well as mutant zebrafish with dysregulated β-catenin activity, the present invention provides for wnt/β-catenin regulation required for several aspects of liver development and adult tissue homeostasis.

Progressive loss of APC did not have a linear effect on liver size during embryonic development. Loss of APC led to increased cytoplasmic and nuclear β-catenin accumulation. Although in the APC+/− embryos this resulted in higher hepatocyte numbers, the complete absence of β-catenin regulation in the APC−/− mutants caused increased apoptosis and a failure to develop differentiated endodermal organs. The use of heat-shock inducible transgenic fish as reported herein demonstrates that the functional requirements of wnt signaling in endodermal progenitors vary during embryonic development. Surprisingly, although excess wnt/β-catenin signaling in early somatogenesis (~1 somite to 5 somites) could inhibit appropriate liver development, wnt8 activation at 10 somites led to increased liver. Enhanced progenitor proliferation mediated by elevated wnt/β-catenin signaling (10 somites to 24 hpf) can expand the progenitor pool rapidly and exponentially, resulting in the large differences in liever size and cell number observed in wnt8 and APC+/− embryos. After the differentiated liver has formed, elevated wnt signaling (48 hpf) again enhances in hepatocyte proliferation and overall organ growth. Together, these data indicate several stage-dependent requirements for regulation of wnt signaling for the proper specification and development of the liver.

The observations support a biphasic wave model of the effects of wnt/β-catenin signaling on endodermal progenitors and specified hepatocytes. Additionally, this reconciles discrepancies in the reports of the effects of wnt/β-catenin signaling on endodermal development, specifically in the liver. During early somitogenesis, high levels of wnt signalin are detrimental to liver specification and development. The APC−/− mutant embryos illustrate the need for some repression of β-catenin signaling for appropriate endodermal progenitors. After endodermal fate is assigned, wnt is required to initiate progenitor cell expansion and organ growth as demonstrated herein. Elevated β-catenin signaling in the APC+/− embryos confers a growth advantage at this stage that is reflected by the increased number of proliferating hepatoblasts and the subsequent enhancement of liver cell number.

A provocative finding presented herein was that wnt/β-catenin signaling can alter developmental fate of unspecified endodermal progenitors. The effect of wnt/β-catenin induction on the subsequent differentiation of endodermal organs was striking in the heat-shock inducible wnt8 embryos. Wnt/β-catenin signaling altered both the longitudinal axial zone of liver specification and shifter the distribution of progenitors to liver-specific cell fates. Most notably, excess wnt signaling appeared to be particularly unfavorable to the development of the pancreas. The zone of endodermal cells competent to respond to liver-modulated signals may expand, truncating the region normally available for pancreas development. Alternatively, if bipotential hepato-pancreatic progenitors exist, biased pressure to differentiate into liver cell fates would effectively diminish the number of progenitors available to produce the pancreas. In embryo explant analysis, ventral foregut endoderm was shown to activate pancreatic gene programs in the absence of liver induction signals, such as fibroblast growth factor, suggesting that bipotential cells exist. Deutsch et al., 128 Devel. 871-81 (2001). The nature of these populations of multipotent progenitors may be manipulated therapeutically. Although hepatic progenitors capable of differentiating into both hepatocyts and cholangiocytes have been described (Strick-Marchand et al., 101 P.N.A.S. USA 8360-65 (2004)), no examination of the plasticity of the progenitors with respect to pancreatic differentiation has been completed.

The present invention introduces the development of partial hepatectomy as a novel technique in the zebrafish that allows for regeneration studies in the liver. The zebrafish liver regenerates to its original size within seven days, comparable with the kinetics of murine liver regrowth. The size of the zebrafish and the complexity associated with resection of an unencapsulated organ preclude an exact quantitative analysis of liver regrowth based on liver/body weight ratios, but the development of the en-bloc dissection analysis as detailed herein, as well as thorough histological characterization at several stages during regeneration allow accurate and detailed analysis. For example, using the wnt-reporter fish, the present work demonstrates in vivo that wnt signaling is activated within the first 24 hours at the resection margins.

Additionally, the present invention provides the first example that the activation of wnt/β-catenin signaling can enhance the rate of liver regeneration. Analysis of wnt8 transgenic and APC+/− fish revealed that increased levels of nuclear β-catenin led to enhanced cell proliferation and accelerated liver regrowth. Furthermore, the regeneratice advantage is evolutionarily conserved following hepatectomy in APCMin/+ mice. (Murine liver resections were performed as described in Green & Puder, 16 J. Investigational Surgery 99-102 (2003). Thus, the present invention provides for the manipulation of the wnt/β-catenin pathway as a way to enhance liver regeneration in patients, either after liver resection or during recovery from acute liver failure induced by toxins such as acetaminophen.

As shown here, wnt/β-catenin signaling effects several endodermal and liver cell populations during liver development, and this program is re-activated to regulate liver regeneration. Wnt/β-catenin signaling has a well-documented involvement in a variety of forms of hepatic neoplasia: hepatoblastomas show frequent mutation of APC, and cholangiocarcinomas and HCC demonstrate alterations in β-catenin, AXIN, and GSK-3β. This suggests that just as wnt/β-catenin signaling can regulate hepatic cell fate at several stages during liver development, wnt/β-catenin signaling can contribute to carcinogenesis within several populations of hepatic cell types. Understanding the development effects of wnt/β-catenin signaling on these cell populations can uncover mechanisms of carcinogenesis and how it can be inhibited in each cell type. The zebrafish model provides a unique opportunity for the identification of novel therapeutics to modulate wnt signaling. A chemical genetic screen for modifiers of wnt-mediated regulation of call growth during embryogenesis is currently underway; compounds identified by this method may be further evaluated for conserved function during adult zebrafish liver regeneration and in modulation of carcinogenesis in APC+/− fish as well as in chemically-induced zebrafish models of liver cancer. Thorough analysis of the function of wnt/β-catenin signaling in liver development, hepatocyte proliferation and in carcinogenesis in zebrafish, as a large-scale chemical screening, enhances the ability to more effectively diagnose and treat cancer.

Another embodiment of the present invention provides for compositions and methods that modulate vertebrate tissue growth or regeneration via the prostaglandin signaling pathway. For example, prostaglandin E2 enhances vertebrate tissue regeneration. A chemical screen in zebrafish identified the prostaglandin signaling pathway as a potent modifier of liver growth during embryonic development. Incubation of embryos with cox1-, cox2-, or dual-specific inhibitors caused a marked reduction in liver size by 72 hpf compared to wild-type controls, while exposure to dimethylprostaglandin E2 (dmPGE2) enhanced liver development. Morpholino knock-down of either cox1 or cox2 similarly inhibited liver growth, and was fully rescued by exposure to exogenous dmPGE2. As many molecular pathways controlling embryonic development mediate tissue homeostasis in the adult, the effects of prostaglandin signaling during liver regeneration were examined. A novel methodology was devised to consistently resect ⅓ of the liver of live zebrafish; following administration of tricaine anesthetic, a small incision was made in the abdomen, just posterior to the heart, and the inferior lobe of the tri-lobular liver was removed using microdissection scissors. Fish were revived and allowed to heal in fish water.

To test the requirement of functional prostaglandin signaling during regeneration, fish were exposed to the dual-specific cox inhibitor, indomethacin, from hour 6 to hour 18 following partial hepatectomy. Indomethacin significantly reduced liver re-growth at day 1 and day 3 compared to controls, and failed to regenerate fully by day 5 post-resection. Additionally, indomethacin exposure resulted in altered architecture of the liver both immediately in the region of the resection margin and throughout the un-injured portions for the organ. Cox inhibition also prohibited wound healing at the incision site.

Exposure to dmPGE2 following resection led to enhanced liver regrowth with noted increases in liver vascularity compared to untreated fish. This enhancement was seen as early as day 1 post-resection and led to a faster complete regeneration of the organ. In addition, a more rapid wound healing of the connective tissue was observed. Regulation of prostaglandin E2 levels may function to repair/regrow a variety of tissue types, such as cardiac, bone, and wound repair.

Additionally, the prostaglandin pathway interacts with wnt signaling: dmPGE2, an activator of the prostaglandin pathway, was found to enhance wnt signaling in the developing brain, liver, and gut, while indomethicin resulted in the virtual absence of wnt signaling. Furthermore, cox inhibition could mitigate the growth-promoting effects of wnt activation on liver development and liver regeneration. Results suggest that the prostaglandin pathway is directly affecting the transcription activity of β-catenin, the central mediator of the wnt pathway. Similarly, wnt signaling can also modulate formation and recovery of hematopoietic stem cells, as described in WO 07/112084. As with the liver, wnt-mediated enhancement of HSC number can be blocked by inhibition of prostaglandin signaling. This suggests that the interaction of the wnt and prostaglandin pathways is conserved in growth and repair of a number of tissues. The wnt signaling pathway is a potentially attractive target for therapeutic manipulation: activation of the pathway enhances tissue growth and regeneration after injury, conversely inhibition might be important in cancer therapy. Wnt inhibitors discovered to date, however, have not yet been fully developed for clinical use, perhaps due to toxicity or side-effects. Using prostaglandins or prostaglandin inhibitors to regulate wnt signaling provide an alternative, balanced approach: wnt activation could provide a benefit in the acute repair phase after injury, while inhibition of prostaglandins might serve to prevent unwanted effects of wnt signaling.

Tissue growth modulators of the present invention that affect the prostaglandin pathway such that tissue growth is inhibited include Indomethacin, NS398, SC560, Celecoxib, Sulindac, Fenbufen, Aspirin, Naproxen, Ibuprofen, AH6809 (EP1/2 antag), and AH23848 (EP4 antag).

Tissue growth modulators that affect the prostaglandin pathway such that tissue growth is enhanced include dmPGE2, PGE2, PGI2, Linoleic Acid, 13(s)-HODE, LY171883, ONO-259, Cay10397, Eicosatrienoic Acid, Epoxyeicosatrienoic Acid, and Arachidonic Acid.

Tissue growth modulators that affect the wnt pathway such that growth is inhibited include Kenpaullone (HDAC effect, not GSK3b), Valproic Acid, (HDAC effect, not GSK3b), and Soluble dkk.

Conversely, tissue growth modulators that affect the wnt pathway such that growth is enhanced include BIO, LiCl, and Soluble wnt ligand.

Additionally, tissue growth modulators that affect cAMP/PI3K/AKT second messenger modifiers—acting downstream of initial prostaglandin signaling such that tissue growth is inhibited include, H89, PD98059, KT5720, U0126, LY294002 and Wortmannin.

Tissue growth modulators that affect cAMP/PI3K/AKT second messenger modifiers—acting downstream of initial prostaglandin signaling such that tissue growth is enhanced include Forskolin, 8-bromo-cAMP, and Sp-5,6,-DCI-cBiMPS.

Other tissue growth modulators that may act downstream of initial prostaglandin signaling include Ca2+ second messenger modifiers. Those that inhibit tissue growth include BayK 8644 and Thioridazine. Those that are considered growth enhancers include Bapta-AM, Fendiline, Nicardipine, Nifedipine, Pimozide, Strophanthidin, and Lanatoside.

The NO/Angiotensin signaling modifiers pathways can interact with prostaglandin and wnt signaling according to the present invention. Those that inhibit tissue growth include L-NAME, Enalapril, Captopril, AcSDKP, Losartan, Telimasartan, Histamine, Ambroxol, Chrysin, Cycloheximide, Methylene Blue, Epinephrine, Dexamethazone, Proadifen, Benzyl isothiocyanate, and Ephedrine.

NO/Angiotensin modifiers that can interact with prostaglandin and wnt signaling to enhance tissue growth include L-Arg, Sodium Nitroprusside, Sodium Vanadate, and Bradykinin.

Early experimental evidence suggests that liver growth may be inhibited by tissue growth modulators such as Norethindrone, 3-estradiol, Beta-Carotene, and BMS189453. Conversely, liver growth was enhanced by Flurandrenolide, All-trans retinoic acid, Vitamin D, and Retinol.

Prostaglandin E2 (PGE2), a product of cyclooxygenase (COX), exerts functions by binding to four G protein-coupled receptors (EP1-EP4). Thus, tissue growth modulators of the present invention include PGE2 receptor agonists and PGE2 receptor antagonists.

EP4-selective agonists include ONO-AE1-734 (methyl-7-[(1R, 2R, 3R)-3-hydroxy-2-[(E)-(3S)-3-hydroxy-4-(m-methoxymethylphenyl)-1-butenyl]-5-oxocyclopenthl]-5-thiaheptanoate), ONO-AE1-437, ONO-AE1-329, ONO-4819 (each from Ono Pharma. Co., Osaka, Japan), APS-999 Na (Toray Indus., Inc., Tokyo, Japan), AGN205203, an analog from the 8-azapiperidinone series of EP4 agonists (Allergan, Inc., Irvine, Calif.), L-902,688 (Merck Frosst Canada, Ltd.), 1,6-disubstituted piperidin-2-one, 3,4-disubstituted 1,3-oxazinan-2-one, 3,4-disubstituted 1,3-thiazinan-2-one and 4,5-disubstituted morpholin-3-one derivatives, see U.S. Pat. No. 7,053,085 (Merck & Co. Inc, Rahway, N.J.).

Conversely, EP4-selective antagonists include ONO-AE3-208 (4-{4-Cyano-2-[2-(4-fluoronaphthalen-1-yl) propionylamino] phenyl} butyric acid) (Ono Pharma. Co., Osaka, Japan), CJ-023,423 (N-[({2-[4-(2-ethyl-4,6-dimethyl-1H-imidazo [4,5-c] pyridin-1-yl) phenyl]ethyl}amino) carbonyl]-4-methylbenzenesulfonamide) (Pfizer), BGC20-1531 (BTC Intl, Ltd.), AH23848, ((4Z)-7-[(rel-1S,2S,5R)-5-((1,1'-Biphenyl-4-yl) methoxy)-2-(4-morpholinyl)-3-oxo-cyclopentyl]-4-heptenoic acid hemicalcium salt hydrate), AH22921 ([1α(Z),2βa,5α]-(±)-7-[5-[[(1,1'-biphenyl)-4-yl] methoxy]-2-(4-morpholinyl)-3-oxocyclopentyl]-5-heptenoic acid) (GlaxoSmithKline), L-161,982 (N-[[4'-[[3-Butyl-1,5-dihydro-5-oxo-1-[2-(trifluoromethyl) phenyl]-4H-1,2,4-triazol-4-yl]methyl][1,1'-biphenyl]-2-yl]sulfonyl]-3-methyl-2-thiophenecarboxamide) (Merck Frosst Ltd., Canada).

EP2-selective agonists include ONO-AE1-259, ONO-8815Ly, ONO-8815, (L-lysine(Z)-7-[(1R,2R,3R,5R)-5-chloro-3-hydroxy-2[(E)-(S)-4-(1-ethylcyclobutyl)-4-hydroxy-1-butenyl] cyclopentyl]-5-heptenoate) (Ono Pharma. Co., Osaka, Japan), AH13205 (trans-2-[4-(1-hydroxyhexyl) phenyl]-5-oxocyclopentane-heptanoic acid) (GlaxoSmithKline).

Several prostaglandin derivatives exhibit relative potency to increase liver growth as shown on the following chart:

| Prostaglandin Derivatives | |
|---|---|
| (⇑ indicates relative potency to increase liver growth): | |
| ⇑ | PGE2 |
| ⇑ | PGI2 |
| ⇑⇑⇑ | 16-phenyl tetranor PGE2 |
| ⇑⇑ | 16,16-dimethyl PGE2 |
| ⇑⇑ | 19(R)-hydroxy PGE2 |
| ⇑⇑ | 16,16-dimethyl PGE2 p-(p-acetamidobenzamido) phenyl ester |
| ⇑⇑ | 9-deoxy-9-methylene-16,16-dimethyl PGE2 |
| ⇑⇑ | PGE2 methyl ester |
| ⇑⇑ | Butaprost |
| ⇑ | 15(S)-15-methyl PGE2 |
| ⇑ | 15(R)-15-methyl PGE2 |
| ⇑ | 20-hydroxy PGE2 |
| ⇑ | 11-deoxy-16,16-dimethyl PGE2 |
| ⇑ | 9-deoxy-9-methylene PGE2 |
| | 9-keto Fluprostenol |
| ⇑ | PGE2 serinol amide |
| ⇑ | Sulprostone |
| | 17-phenyl trinor PGE2 |
| | 8-iso-15-keto PGE2 |
| | 8-iso PGE2 isopropyl ester |
| toxic | 5-trans PGE2 |

Other example molecules involved in the wnt pathway, which that may serve as modulators encompassed within the scope of the present invention, have been reported. See, e.g., Barker & Clever, 5 Nature Rev. Drug Discovery 997-1014 (2007); Janssens et al., 24 Investigational New Drugs 263-80 (2006). It should be noted, however, that there have been significant adverse side effects reported with attempts to directly suppress wnt signaling in cancer patients. Barker & Clever, 2007. Hence, as the present invention suggests, indirect modulation of the wnt signaling pathway via the prostaglandin pathway may prove more efficacious in therapeutic development.

The tissue growth modulators within the scope of the present invention may be identified in a variety of ways, such as the zebrafish genetic system. The zebrafish (*Danio rerio*) is an excellent genetic system for the study of vertebrate development and diseases. See e.g., Hsia & Zon, 33(9) Exp. Hematol. 1007-14 (2005); de Jong & Zon; 39 Ann. Rev. Genet. 481-501 (2005); Paffett-Lugassy & Zon, 105 Meth. Mol. Med. 171-98 (2005); Haffner & Nusslein-Volhard, 40 Int'l J. Devel. Biol. 221-27 (1996). The embryo developing externally is transparent and organs can be easily visualized. Zebrafish and mammals share many of the same gene programs in development. When zebrafish mate, they give rise to large numbers (100-200 weekly) of transparent embryos. Many embryos can be placed in a relatively small space, and there is a short generation time (about 3 months). Large-scale screens have generated more than 2000 genetic mutants with specific defects that affect virtually every aspect of embryogenesis. Driever et al., 123 Devel. 37-46 (1996); Eisen, 87 Cell 969-77 (1996). Many of the blood mutants have been useful in describing key events in hematopoeisis. Dooley & Zon, 10 Curr. Op. Genet. Devel. 252-56 (2000). Zebrafish have been used to perform whole organism-based small molecule screens because large numbers of the embryos can be arrayed into microtiter plates containing compounds from a chemical library. For example, Peterson and colleagues tested 1,100 compounds for developmental defects. Peterson et al., 97 P.N.A.S. USA 12965-69 (2000). From this screen, about 2% of the compounds were lethal, and 1% caused a specific phenotype. For example, one compound suppressed formation of inner ear structures called otoliths, but caused no other defects.

It is also possible to screen for chemical suppressors of mutant phenotypes. Peterson et al., 22 Nat. Biotech. 595-99 (2004); Stern et al., 1 Nat. Chem. Biol. 366-70 (2005). In one such screen, chemicals were found to rescue the gridlock mutant, a model of congenital coarctation of the aorta. Peterson et al., 2004. The mechanism of this rescue involved the induction of VEGF which corrected the angiogenesis defect. These data demonstrate that highly potent and specific compounds can be identified using zebrafish.

Further regarding zebrafish, a high-density genetic map has been constructed that includes microsatellite markers, genes, and expressed sequence tags (ESTs). Knapuk et al., 18 Nat. Genet. 338-43 (1998); Shimoda et al., 58 Genomic 219-32 (1999); Kelly et al., 10 Genome Res. 558-67 (2000); Woods et al., 20 Genome Res. 1903-14 (2000). A full-length cDNA project has also been undertaken as an extension to the zebrafish EST project. A dense RH map has been constructed and integrated with data for the genome sequencing project at the Sanger Center. An important web resource supported by the NIH is the zebrafish information network (ZFIN), a focal point for the community. A stock center and supportive laboratory called the Zebrafish International Resource Center (ZIRC) also greatly helps the field. The Sanger Center is sequencing the zebrafish genome.

Using the techniques described herein, wild-type and transgenic zebrafish may be exposed to numerous compounds to assess the effect of the compound as modulators of the prostaglandin and/or wnt/β-catenin signaling pathways. For example, test compounds can be administered to transgenic fish harboring an exogenous construct containing the expression sequence of a reporter protein. By comparing the expression of the reporter protein in fish exposed to a test compound to those that are not exposed, the effect of the compound on the modulation of the prostaglandin signaling pathway may be determined. Similarly, comparing the expression of the reporter protein in fish exposed to a test compound to negative controls, the effect of the compound on the modulation of the wnt/β-catenin signaling pathway can be assessed. Test compounds can act as either inhibitors or activators of the reporter gene. Importantly, modulators of the individual pathways may then be combined and contacted with reporter fish and the expression of the reporter protein compared with the appropriate positive and negative controls. In this manner, modulators that are useful as drugs for treating conditions associated with wnt/β-catenin signaling pathway which may be affected by modulators of the prostaglandin pathway, as described herein, are identified.

The modulators of the present invention include those that directly modulate the wnt signaling pathway; modulate the prostaglandin pathway to effect modulation of the wnt signaling pathway; or modulate the downstream effects of prostaglandin to modulate wnt. Additionally, these modulators may be combined to "fine tune" the signal. For example, a wnt signaling activator may be employed until the desired enhancement is noted, followed by a prostaglandin inhibitor to limit the effects of the wnt activator. Or, for example, a low-dose wnt activator could be combined with a low-dose prostaglandin activator to avoid toxicity. Thus, the interactions of the modulators of the wnt and prostaglandin signaling pathways may be used in any direction or in any combination to elicit a desired response while limiting toxicity or exuberant growth. The modulators may be used simultaneously or sequentially.

Patients may benefit from the present invention in several ways: for example, patients undergoing liver resection surgery may regain their hepatic function faster, decreasing complications and hospitalization. Conceivably, patients receiving a liver transplant may have a higher rate of organ survival. As applied to other aspects of organ and tissue regeneration, for example, enhanced recovery in the wound healing process, after myocardial infarction, and after bone fracture may be positively impacted. Additionally, for example, subjects suffering from traumatic injury, drug toxicity, poisoning (e.g., *Amanita* ingestion), industrial toxins, surgery, liver donation, cancer, skin grafts, burns, etc., may have the modulators of the present invention added to their treatment regimen. The present growth modulators may be useful on any tissue capable of regeneration, repair, or regrowth, including hematopoietic stem cells, liver, skin, or vessels.

Direct ex vivo administration of modulators may enable significant in vivo tissue development or regenerations, such that even smaller amounts of tissue can then be enough in transplantation. Origin of such tissue is not limited. Alternatively, a tissue source sample, such as skin, may be harvested and then stored immediately in the presence of a modulator, such as PGE2, and initially incubated (prior to implantation) in the presence of the modulator before introduction into a subject.

Additionally, one or more modulator might be used to enhance the function of the tissue source. For example, modulating the wnt/PGE2 pathway may hasten a graft's ability to assume its physiological role and consequently lead to a decrease in the time during which the subject has insufficient tissue (for example liver tissue) thus reducing complication risks. Additionally, a modulator could be administered to a living donor after removal of the tissue to speed healing.

The tissue growth modulators may be used in vivo to enhance tissue growth and ex vivo to increase tissue growth. This is accomplished by administering one or more of the compounds to a subject or to the resected tissue. For example, in reconstruction of the uterus, excised tissue may be treated with tissue growth modulator in the context of a biocompatible scaffold (see e.g., U.S. Pat. No. 704,057, "Tissue engineered uterus" issued to Atala et al.) to provide a enhance autologous tissue growth before implantation.

Various kits and collection devices are known for the collection, processing, and storage of source cells are known in the art. The modulators of the present invention may be introduced to the cells in the collection, processing, and/or storage. Thus, not being limited to any particular collection, treatment, or storage protocols, an embodiment of the present invention provides for the addition of a modulator, such as, for example, wnt activators, PGE2 or dmPGE2, or their analogs, cAMP activators, etc., to a tissue sample. This may be done at collection time, or at the time of preparation for storage, or upon thawing and before implantation.

The method of the invention thus provides the following benefits: (1) Allows transplantation to proceed in patients who would not otherwise be considered as candidates because of the unacceptably high risk of failed engraftment or failure of primary graft function; (2) Reduces the size of the donor tissue required to generate a minimum acceptable harvest; (3) Reduces the incidence of primary and secondary failure of engraftment by increasing the tissue sample available for transplantation; and (4) Reduces the time required for primary engraftment by enhancing the growth of the implanted tissue.

The modulators of the invention, e.g., modulators that inhibit tissue growth, may also be of use in treating subjects suffering from hyperproliferative disorders including those of the hematopoietic system or other cancers. In particular, modulators may be useful in therapies to treat liver disease.

The modulators of the present invention also include derivatives of such modulators. Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled modulators, conjugates of modulators (e.g., biotin or avidin, with enzymes such as horseradish peroxidase and the like, with bioluminescent agents, chemoluminescent agents or fluorescent agents). Additionally, moieties may be added to the modulator or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. Derivatives, as used herein, also encompasses prodrugs of the modulators, which are known to enhance numerous desirable qualities of pharmaceuticals (e.g., solubility, bioavailability, manufacturing, etc.).

The compounds or agents of the present invention can be contained in pharmaceutically acceptable formulations. Such a pharmaceutically acceptable formulation may include a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

When the agents or compounds are delivered to a patient, they can be administered by any suitable route, including, for example, orally (e.g., in capsules, suspensions or tablets) or by parenteral administration. Parenteral administration can include, for example, intramuscular, intravenous, including direct administration into the portal vein, including direct administration into the portal vein, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. Administration can be local or systemic as indicated. Agents can also be delivered using viral vectors, which are well known to those skilled in the art.

Both local and systemic administration are contemplated by the invention. Desirable features of local administration include achieving effective local concentrations of the active compound as well as avoiding adverse side effects from systemic administration of the active compound. In a preferred embodiment, the antagonist is administered locally. Localized delivery techniques are described in, for example, 51 J. Biomed. Mat. Res. 96-106 (2000); 100(2) J. Control Release 211-19 (2004); 103(3) J. Control Release 541-63 (2005); 15(3) Vet. Clin. North Am. Equine Pract. 603-22 (1999); 1(1) Semin. Interv. Cardiol. 17-23 (1996)

The pharmaceutically acceptable formulations can be suspended in aqueous vehicles and introduced through conventional hypodermic needles or using infusion pumps.

The amount of agent administered to the individual will depend on the characteristics of the individual, such as general health, age, sex, body weight and tolerance to drugs as well as the degree, severity and type of rejection. The skilled artisan will be able to determine appropriate dosages depending on these and other factors.

Several embodiments will now be described further by non-limiting examples.

EXAMPLES

Example 1

Techniques Associated with the Zebrafish Model

Zebrafish husbandry: Zebrafish were maintained according to IACUC protocols. The LFABP:GFP (a gift from G. M. Her & J. L. Wu, Nat'l Cheng Kung Univ., Taiwan), gut:GFP, hs:wnt8-GFP, hs:dnTCF-GFP, and hs:dkk-GFP transgenic lines were used. Dorsky et al., 2002: Her et al., 538 FEBS Lett 125-133 (2003); Lewis et al., 131 Devel. 1299-1308 (2004); Ober et al., 120 Mech. Devel. 5-18 (2003); Stoick-Cooper et al., 134 Devel. 479-89 (2007); Weidingder et al., 15 Curr. 489-500 (2005). Genotyping for APC mutants was performed as described. Hurlstone et al., 2003.

Heat shock activation/repression of wnt signaling: Embryonic heat-shock experiments were conducted at 38° C. for a duration of 20 minutes unless otherwise noted. Genotype was determined by the presence of GFP fluorescence at three hours post heat-induction, non-fluorescence (wild-type) siblings were used as controls.

Morpholino knockdown: MO (Gene Tools, LLC, Philomath, Oreg.) directed against zebrafish β-catenin, wnt2b, wnt3, wnt5, wnt8, and wnt11 (Buckles et al., 121 Mech. Devel. 437-47 (2004); Lekven et al., 1 Cell Devel. 103-14 (2001); Lele et al., 30 Genesis 190-94 (2001); Lyman Gingerich et al., 2004; Ober et al., 442 Nature 688-91 (2006)), or mismatched controls were injected into zebrafish embryos at the one-cell stage at a concentration of 40 µM.

In situ hybridization: Paraformaldehyde (PFA)-fixed embryos were processed for in situ hybridization using standard zebrafish protocols such as those found on the internet at, for example, ZFIN: The Zebrafish Model Organism Database (hosted by the Univ. Oregon, Eugene, Oreg.). The following RNA probes were used to detect alterations in endodermal and liver development: GFP, LFABP, sterol carrier protein, transferrin, foxA3, insulin, trypsin, and IFABP. Changes in expression compared to wild-type controls are reported as the # altered/# scored per genotype; a minimum of three independent experiments were conducted per analysis.

Immunohistochemistry: Embryos, adults, and en bloc abdominal sections were fixed with PFA, paraffin embedded, and cut in 40 µm serial step-sections for histological analysis. Hematoxylin/eosin staining was performed on alternate sections using standard techniques. Antibodies to β-catenin (1:100) (BD 610154, BD Transduction Laboratories™, San Jose, Calif.), TUNEL (Chemicon/Millipore, Billerica, Mass.), BrdU (1:2000) (clone BU-33, B2531, Sigma-Aldrich, St. Louis, Mo.) and PCNA (1:80) (Clone PC10, NA03, Calbiochem/EMD Chemicals, Inc., San Diego, Calif.) were visualized by DAB and counterstained with hematoxylin or methylene green.

Caspase Assay: Single embryos were manually dissociated in lysis buffer and centrifuged. The supernatant (100 ml) was used for the Caspase-Glo® 3/7 Assay System according to the manufacturer protocol (Promega Corp., Madison, Wis.). DNA isolated from the cell pellet was used to confirm APC genotype.

Confocal Microscopy: GFP transgenic zebrafish embryos were embedded in 1% low-melting point agarose containing 0.4 mg/ml Tricaine-S in glass-bottom culture dishes for visualization through a Zeiss LSM Meta confocal microscope (Carl Zeiss MicroImaging, Inc., Thornwood, N.Y.).

Flow Cytometry Analysis: Individual embryos were manually dissociated in 0.9% PBS and examined for GFP fluorescence and forward scatter. Genotyping for APC was performed by PCR on excess cells following FACS anaysis.

Liver Resection: Folling administration of tricaine anesthetic, ⅓ partial hepaectomy of the adult zebrafish liver was performed under brightfield imaging on a dissection microscope. An incision was made using microdissection scissors posterior to the heart on the left lateral portion of the abdomen. Forceps were then used to resect the entire length of the inferior lobe.

Example 2

Zebrafish Tumor Model

Although zebrafish are a valuable vertebrate model to study carcinogenesis, noninvasive imaging remains challenging because adult fish are not transparent. Tumors can be readily detected in vivo, however, using high-resolution microscopic ultrasound. This technique facilitates tissue perfusion calculations, cellular aspirates, tumor progression analysis, and responses to treatment. Ultrasound biomicroscopy allows longitudinal studies of tumor development and real-time assessment of therapeutic effects in the zebrafish model. The visualization techniques employed herein are described by Goessling et al., 4(7) Nature Methods 551-53 (2007).

Figure 10A:
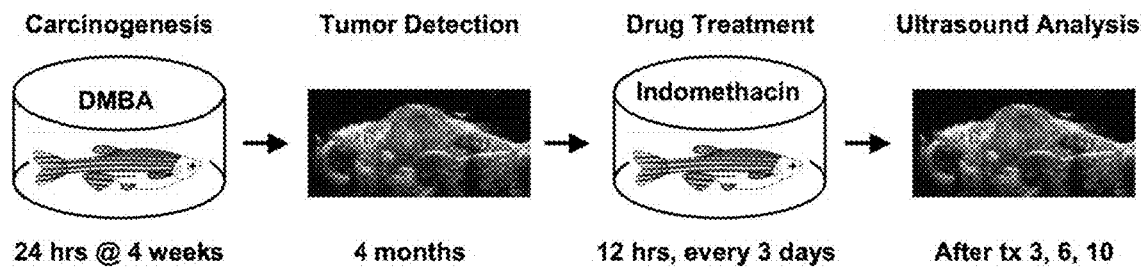
FIGS. 10A-10C collectively show the effect of prostaglandin inhibition on liver tumor growth.

As shown in FIG. 10, zebrafish were exposed to DMBA at three and four weeks of age. Tumor occurrence was monitored over about five months. Tumors were identified by ultrasound biomicroscopy. The cancerous fish were then treated with indomethacin for twelve hours over night, every three days for one month, and the tumors visualized as described. Goessling et al., 2007. In representative fish, tumor size increased and architecture changed after three treatments. After six treatments, the solid portion of the tumor decreased in size, and an area of liquefaction appeared in the posterior aspect of the abdomen, suggestive of tumor necrosis. After ten treatments, the tumor had shrunk substantially, and appeared diminished in size compared to the initial ultrasound. After one month of drug treatment, the fish appeared healthy, but were sacrificed to confirm the presence of cancer by histology. These observations demonstrate the effect of prostaglandin inhibition on liver tumor growth, and the successful chemotherapy of fish.

Figure 10B:
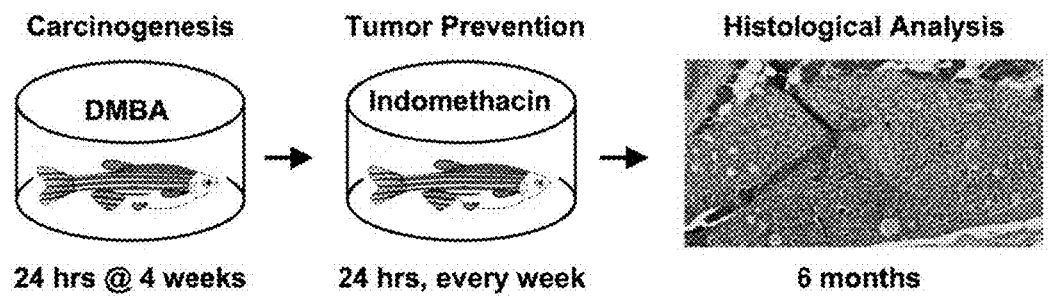
Figure 10C:
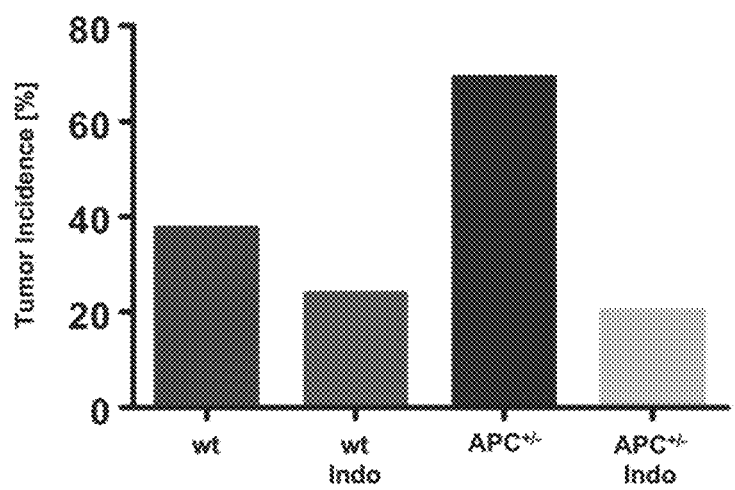
Figure 11A:
FIGS. 11A-11B collectively show the effect of simultaneous modulation of wnt and prostaglandin signaling pathway on mouse bone marrow transplantation. This figure illustrates how wnt activation by BIO enhances early spleen colony formation following bone marrow transplantation. Indomethacin blocks this effect.
Figure 11B:
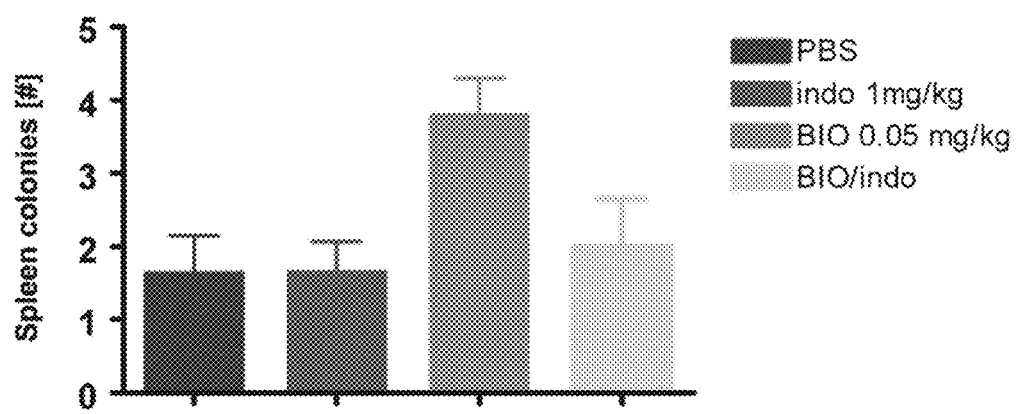
Figure 12:
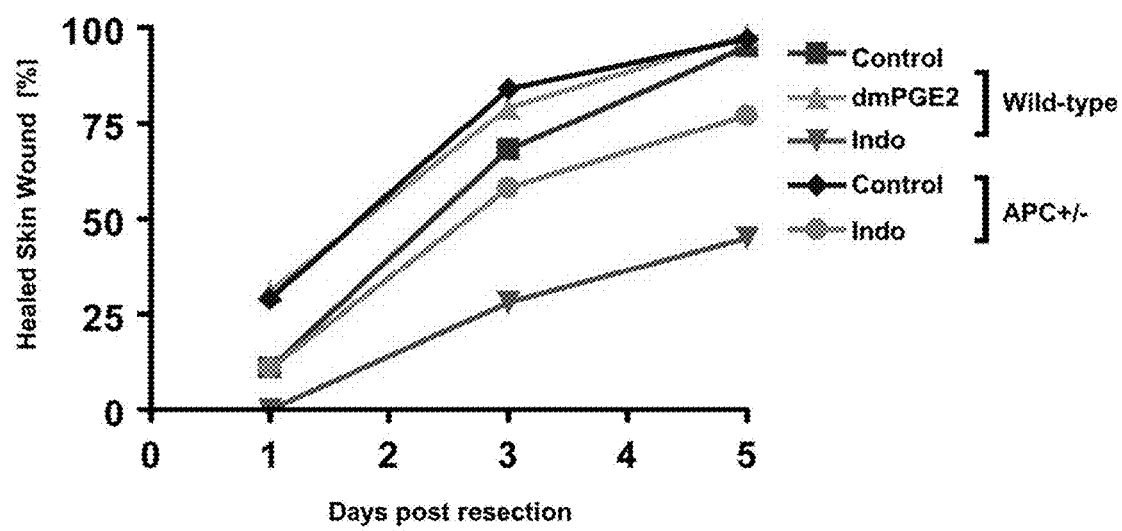
FIG. 12. Effect of prostaglandin modulation and wnt activation on wound healing in zebrafish. Skin wounds following partial hepatectomy heal faster and to a greater extent with PGE2 as well as in APC+/− fish. Wound healing is severely inhibited after administration of indomethacin.

In another experiment, detailed in FIG. 10B and FIG. 10C, fish were treated every week for tumor prevention. Here, treatment with the carcinogen led to liver tumors in wild-type fish, and to twice as many tumors in APC+/− mutant fish. Weekly treatment with indomethacin decreased tumor formation in both wild-type, but especially in APC+/− fish.

The invention claimed is:

1. A pharmaceutical composition comprising at least one $PGE_2$ receptor agonist, a wnt pathway activator, and hematopoietic stem or progenitor cells;
   wherein the hematopoietic stem or progenitor cells have been contacted with the $PGE_2$ receptor agonist and the wnt pathway activator ex vivo.

2. The composition of claim 1, wherein the at least one $PGE_2$ receptor agonist comprises at least one prostaglandin signaling pathway activator selected from the group consisting of: $PGE_2$, $PGI_2$, 16-phenyl tetranor $PGE_2$, 16,16-dimethyl $PGE_2$, 19(R)-hydroxy $PGE_2$, 16,16-dimethyl $PGE_2$ p-(p-acetamidobenzamido) phenyl ester, 9-deoxy-9-methylene-16, 16-dimethyl $PGE_2$, $PGE_2$ methyl ester, Butaprost, 15(S)-15-methyl $PGE_2$, 15(R)-15-methyl $PGE_2$, 20-hydroxy $PGE_2$, 11-deoxy-16,16-dimethyl $PGE_2$, 9-deoxy-9-methylene $PGE_2$, PGE serinol amide, and Sulprostone.

3. The composition of claim 1, wherein the wnt pathway activator is selected from the group consisting of a GSK-3 inhibitor and a soluble Wnt ligand.

4. The composition of claim 2, wherein the wnt pathway activator is selected from the group consisting of a GSK-3 inhibitor and a soluble Wnt ligand.

5. The composition of claim 3, wherein the GSK-3 inhibitor is LiCl or 6-bromoindirubin-3'-oxime (BIO).

6. The composition of claim 4, wherein the GSK-3 inhibitor is LiCl or 6-bromoindirubin-3'-oxime (BIO).

7. The composition of claim 3, wherein the soluble Wnt ligand is Wnt2b, Wnt3, or Wnt8.

8. The composition of claim 4, wherein the soluble Wnt ligand is Wnt2b, Wnt3, or Wnt8.

9. A pharmaceutical composition comprising at least one prostaglandin signaling pathway activator or a downstream mediator of the prostaglandin signaling pathway, a wnt pathway activator, and hematopoietic stem or progenitor cells;
   wherein the at least one prostaglandin signaling pathway activator is a $PGE_2$ receptor agonist;
   wherein the downstream mediator of the prostaglandin signaling pathway is selected from the group consisting of: Forskolin, 8-bromo-cAMP, Sp-5,6,-DCI-cBiMPS, Bapta-AM, Fendiline, Nicardipine, Nifedipine, Pimozide, Strophanthidin, and Lanatoside;
   wherein the wnt pathway activator is selected from the group consisting of a GSK-3 inhibitor and a soluble Wnt ligand; and
   wherein the hematopoietic stem or progenitor cells have been contacted with the prostaglandin signaling pathway activator or downstream mediator of the prostaglandin signaling pathway, and the wnt pathway activator ex vivo.

10. The composition of claim 9, wherein the $PGE_2$ receptor agonist comprises at least one prostaglandin signaling pathway activator selected from the group consisting of: $PGE_2$, PGI2, 16-phenyl tetranor $PGE_2$, 16,16-dimethyl $PGE_2$, 19(R)- hydroxy $PGE_2$, 16,16-dimethyl $PGE_2$ p-(p-acetamidobenzamido) phenyl ester, 9-deoxy-9-methylene-16,16-dimethyl $PGE_2$, $PGE_2$ methyl ester, Butaprost, 15(S)-15-methyl $PGE_2$, 15(R)- 15-methyl $PGE_2$, 20-hydroxy $PGE_2$, 11-deoxy-16,16-dimethyl $PGE_2$, 9-deoxy-9-methylene $PGE_2$, PGE serinol amide, and Sulprostone.

11. The composition of claim 1, wherein the at least one $PGE_2$ receptor agonist is an EP2-selective agonist or an EP4-selective agonist.

12. The composition of claim 9, wherein the at least one $PGE_2$ receptor agonist is an EP2-selective agonist or an EP4-selective agonist.

13. The composition of claim 1, wherein the wnt pathway activator enhances tissue growth.

14. The composition of claim 1, wherein the composition consists essentially of at least one $PGE_2$ receptor agonist, a wnt pathway activator, and hematopoietic stem or progenitor cells.

15. The composition of claim 9, wherein the composition consists essentially of at least one prostaglandin signaling pathway activator or a downstream mediator of the prostaglandin signaling pathway, a wnt pathway activator, and hematopoietic stem or progenitor cells.

* * * * *